(12) United States Patent
Miller et al.

(10) Patent No.: US 7,585,957 B2
(45) Date of Patent: Sep. 8, 2009

(54) SITE SPECIFIC SYSTEM FOR GENERATING DIVERSITY PROTEIN SEQUENCES

(75) Inventors: Jeffery F. Miller, Santa Monica, CA (US); Sergei Doulatov, Toronto (CA); Asher Hodes, Los Angeles, CA (US); Min Xu, Los Angeles, CA (US); Mari Gingery, Glendale, CA (US); David W. Martin, Jr., San Francisco, CA (US)

(73) Assignees: The Regents of the University of California, Oakland, CA (US); AvidBiotics Corp, San Francisco, CA (US)

( * ) Notice: Subject to any disclaimer, the term of this patent is extended or adjusted under 35 U.S.C. 154(b) by 276 days.

(21) Appl. No.: 11/197,219

(22) Filed: Aug. 3, 2005

(65) Prior Publication Data

US 2006/0121450 A1 Jun. 8, 2006

Related U.S. Application Data

(60) Provisional application No. 60/598,617, filed on Aug. 3, 2004.

(51) Int. Cl.
 C07H 21/02 (2006.01)
 C12N 5/00 (2006.01)
 C12N 1/00 (2006.01)
 C12N 15/00 (2006.01)
 C40B 40/06 (2006.01)

(52) U.S. Cl. ............... 536/23.1; 435/243; 435/325; 435/320.1; 506/16

(58) Field of Classification Search ........... 536/23.1; 435/243, 325, 320.1; 506/16
See application file for complete search history.

(56) References Cited

U.S. PATENT DOCUMENTS 6,500,644 B1 * 12/2002 Borchert et al. ........... 435/69.1

FOREIGN PATENT DOCUMENTS

WO WO03/052071 A2 6/2003
WO WO03/104470 A2 12/2003
WO WO2004/020627 A2 3/2004

OTHER PUBLICATIONS

Doulatov et al., 2002, Reverse Transcriptase-Mediated Diversity in Host-Parasite Interactions: Tropism Switching by *Bordetella* Baceteriophage, Abstracts of the General Meeting of the American Society for microbiology, 102: 301.*

Doulatov, Sergei, et al. "Tropism switching in *Bordetella* Bacteriophage defines a family of diversity-generating retroelements", *Nature* (2004) 431 (7007):476-481.

Liu, Minghsun, et al. "Genomic and Genetic Analysis of *Bordetella* Bacteriophages Encoding Reverse Transcriptase-Mediated Tropism-Switching Cassettes", *Journal of Bacteriology* (2004) 186(5):1503-1517.

Liu, Minghsun, et al. "Reverse Transcriptase-Mediated Tropism Switching in *Bordetella* Bacteriophage", *Science* (2002) 295(5562):2091-2094.

McMahon, Stephen, A., et al. "The C-type lectin fold as an evolutionary solution for massive sequence variation", *Nature Structural & Molecular Biology* (2005) 12(10):886-892.

Strauch, Eckhard, et al. "Characterization of Enterocoliticin, a Phage Tail-Like Bacteriocin, and Its Effects on Pathogenic *Yersinia enterocolitica* Strains", *Applied and Environmental Microbiology* (2001) 67(12):5634-5642.

Dreiseikelmann, B. "Translocation of DNA across Bacterial Memebranes", *Microbiological Reviews* (1994) 58(3):293-316.

* cited by examiner

*Primary Examiner*—Amber D. Steele
(74) *Attorney, Agent, or Firm*—DLA Piper LLP (US)

(57) ABSTRACT

This invention relates to the diversification of nucleic acid sequences by use of a nucleic acid molecule containing a region of sequence that acts as a template for diversification. The invention thus provides nucleic acid molecules to be diversified, as well as those which act as the template region (TR) and in concert with the TR for directional, site-specific diversification. Further provided are methods of preparing and using these nucleic acid sequences.

9 Claims, 19 Drawing Sheets

Figure 9

*Bordetella* phage

```
TR  CGCTGCTGCGCTATTCGGCGGCAACTGGAACAACACGGCGAACTCGGGTTCTCGCGCTGCGAACTGGAACAACGGGCCGTCGAACTCGAAC
VR  CGCTGCTGCGCTATTCGGCGGCGCCTGGAACGGCGCGGCGCTCTCGGGTTCTCGCGCTGCGCTCTGGTACAGCGGGCCGTCGTTCTCGTTC

TR  GCGAACATCGGGGCGCGCGGCGTCTGTG CCCATCACC TTCTTG
VR  GCGTTCTTCGGGGCGCGCGGCGTCTGTG ACCACCTGA TTCTTGAGtag
```

*Vibrio harveyi* phage

```
TR  ACCGATTCCCGCTTCGCGGGGGCAACTGGAACAATGGCTCGAACGCCGGGCTGGGCGCGCTCAATCTGAACAATGCGCGGTCGAACTCGAA
VR  ACCGGTTCCCGCTTCGCGGGGGCTACTGGAACAATGGCTCGAGCGCCGGGCTGGGCGCGCTCTATCTGAGCTATGCGCGGTCGAACTCGAA

TR  CAATAGCATCGGTTTTCGCCCCGCT CTTGA TGT
VR  CAGTAGCATCGGTTTTCGCCCCGCT TTCTT TGT Gtaa
```

*Bifidobacterium longum*

```
TR  GGTGCAGCGCTTCGGCAACCTCAGGAACGGGGCTGCCTGCGGCGCCTTCGCCGTGAACCTCACGAACGACCTCGCGAATCGCAGGTGGAAC
VR  GGTGCGGCGCTTCGGCCTCCTCTGGGACGGGGCTGCCTGCGGCGCCTTCGCCGTGTACCTCGCGAACGCCCTCGCGAATCGCTGGTGGCAC

TR  ATCGGGGCCGC ATATCC G
VR  CTCGGGGCCGC CTTTCT GCGCTCGGTCGCACGAAGGCGtag
```

*Bacteriodes thetaiotaomicron*

```
TR  TTCCCTGCGTCGGGGTATCGCAACTATTCCAATGGCGGGGCGAACAACGTTGGCAGCTACGGCTACTGTTGGTCGGCGGTTCCGAACAACC
VR  TTCCCTGCGTCGGGGTCTCGCGACTGTTCCGGTGGCGGGGCGAACAGCGTTGGCTTCTACGGCGTCTGTTGGTCGGCGGTTCCGTACAGCC

TR  AGAACAACGGTCGCAACCTGAACTTCAACTCGTCGAACGTGAACCCGTTGAACAACAACAATCGGGCGTACGGGTTTGGG G TGCGTTCT
VR  AGTACCACGGTTGCACCCTGGACTTCTCCTCGTCGTCCGTGTACCCGTTGCTCTACTACTCTCGGGCGTGCGGGTTTGGG T TGCGTTCT

TR  TCCCAAGAAT
VR  TCCCAAGAAtag
```

*Treponema denticola*

```
TR  CCGCGTCAGGCTCTAACCGAGTTAAACGCGGCGGCAGCTGGAACAACAACGCGAACAACTGCACTGTAGGCAAACGGAATAACAACAGTCC
VR  CCGCGTCAGGCTCTGGCCGTGTTTTACGCGGCGGCAGCTGGGCCGGCAGCGCGGACTACTGCGCTGTAGGCGAACGGGTCAACATCAGTCC

TR  TGACAACAGGAACAACAATCTTGGCTTCCGCTTGGCTTG TCGGCCC
VR  TGGCGTCAGGTGCAGCGATCTTGGCTTCCGCCTGGCTTG CCGGCCT taa
```

*Trichodesmium erythraeum #1*

```
TR   GCGGCTCCTGGAACAACTATCCTAGGAGGTGTCGCTCTGCGAACCGCAACAACTATAACTCGGACGAGGCGGACAACAACAATATTGGTTT
VR1  GCGGCTCCTGGCTCAACTATCCTTGGTGGTGTCGCTCTGCGTACCGCTACGACTTTAGCTCGGACGGGGCGGTCATCATCAATTTTGGTTT
VR2  GCGGCTCCTGGTACGACTTTCCTTGGTGGTGTCGCTCTGCGTTCCGCGGCTACTATTTCTCGGTCGAGGCGGTCAACGACTTTGTTGGTTT

TR   TCGTCTTGTGAGTTTCCCCCCCAG C ACTCTT
VR1  TCGTCTTGTGAGTTTCCCCCCCAG G ACTCTTGAAtag
VR2  TCGTCTTGTGAGTTTCCCCCCCAG G ACTCCtga
```

*Figure 9 (cont'd)*

Trichodesmium erythraeum #2

```
TR  GCTCCGTGGCGGTAGCTGGAACCACAATTCTAGACATTGCCGGAGTGCCAGGGGCAACTATAAAAATGCCGACAACCTCAACAACAATAGG
VR  GCTCCGTGGCGGTTGCTGGATCCACAATTCTAGATTTTGCCGGAGTGCCTGGCGCAACTATCTCTATGCCGACTACCTCTCCAACGATAGG

TR  GGTTTTCGAGTCATCTC G TCTTCCCCGGTGGTTTCTGGCTTTCATTCCTAGTATTCTTC
VR  GGTTTTCGAGTCATCTC C TCTTCCCCGGTGGTTTCTGGCTTTCATTCCtagTATTCTTC
```

Nostoc spp. 7120 #1

```
TR   CTGCGGGGCGGCTCCTGGAACAACAATCCTGAAAACTGCCGTTCCGCGTCCCGCAACAACAACAATAGGGCGGAGCGCGACAACATCAACA
VR1  CTGCGGGGCGGCTCCTGGGACGACCTTCCTGAAGGCTGCCGTTCCGCGTCCCGCCTCAGCCTCAATAGGGCGGTGCGCGACCTCATCCTCT
VR2  CTGCGGGGCGGCTCCTGGAGCTCCTCTCCTGTAGTCTGCCGTTCCGCGTCCCGCGGCAACAACGATAGGGCGGGGCGCGTCTACCGCTACT

TR   ACAATATTGGTTTTCGTGTTGTCTGCGCGTTCGGGAG TACTC  TTCAC
VR1  ACAGTTTTGGTTTTCGTGTTGTCTGCGCGTTCGGGAG GATTC  TTCAGtag
VR2  ACGCTGTTGGTTTTCGTGTTGTCTGCGCGTTCGGGAG GACTT  TTCAGtag
```

Nostoc spp. 7120 #2

```
TR  CTGCTGCGCGGTGGTTCGTGGAACAACAATCCCAGGAATTGCCGTTCGGCGAATCGCAACAGGAACGCGCGTGACAACAGGAACAACAACG
VR  CTGCTGCGTGGTGGTTCGTGGAACTACTATCCCAGGGGTTGCCGTTCGTTGAGTCGCCTCAGTAACACGCGCGACGACAGGAACGAGCGCG

TR  TAGGTT T TCGGGTTGTGGTTGTGCGGGGCAG
VR  TGGGTT G TCGGGTTGTGGTTGTGCGGGGCAGGCTTTCTtag
```

Nostoc punctiforme

```
TR   CTGCGGGGCGGTTCCTGGATCAACAATCCTAAAAACTGCCGTTCCGCGTCCCGCAACAACAACAATAGGGCGGAGCGCGACAACATCAACAA
VR1  CTGCGGGGCGGTTCCTGGTTCAACAATCCTGATTTCTGCCGTTCCGCGTCCCGCGTCATCAACAGTTGGGCGGAGCGCGACAACGTCGTCAG
VR2  CTGCGGGGCGGTTCCTGGATCTTCGATCCTGATTACTGCCGTTCCGCGTCCCGCAACCTCAGCTATAGGGCGGAGCGCGACGGCATCCTCAG

TR   CAATATTGGTTTTCGTGTTGTCTGCGCGTTCGGGA TGTC  TCTTCA
VR1  CAATGTTGGTTTTCGTGTTGTCTGCGCGTTCGGGA GGAT  TCTTCAGtag
VR2  CACTCTTGGTTTTCGTGTTGTCTGCGCGTTCGGGA GGAT  TCTTCAGtag
```

*Figure 14* ttcctcgtgctttacggtatcgcgctcccgattcgcagcgcatcgcctctatcgcctttgacgagttcttctga
F L V L Y G I A A P D S Q R I A F Y R L L D E F F tcgttctcgttcgcttcttcgggcgcgcgtctgtgaccacctgattcttg
S F S F A F F G A R G V C D H L I L

Figure 15

```
NpTR                                      CTGCGGGGGCGGTTCCTGGATCAACAATCCTAAAACTGCCGTTCCCGCTTCCCGCCAACAACAACAACAATAGGGGCCAGCCCGACAACATCAACA
N1TR                                      CTGCCGGGGCGGTTCCTGGAACAACAATCCTGAAAACTGCCGTTCCCGCTTCCCGCCAACAACAACAACAATAGGGGCCAGCCGACAACATCAACA
N2TR      CTGCTGCGCGGTGGTTCGTTGGAACAATCCCAGGAATTGCCGTTCGGCGAACAGAACGCGTGACAACAGAAGAACA
T1TR      GCGGCTCCTGGAACAACTATCCTAGGAGTGTCGCTCTGCGAACCGCAACAACTATAACTCGGACGAGCGGACAGAACGAG
CpTR      CCTTTTCGTTGCGCGGGGTTCGTGGAACAAATCTGCCAATCTGTCTTGCTTCTGCCGGAACAACAACAATCCGACAACAGGAACA
PpTR GATCTGCCCGTGCGCGTTGCGCGGCGTTCCTGGAACAATCTCGTTGCTCTGCCGGAACAACAACAATCATCCGGCGAACAGGAACA

NpVR1 CTGCGGGGGCGGTTCCTGGTTCAACAATCCTGATTTCTGCCGTTCCCGCGTCATCAACAGTTGGGCGGAGCGCGACAACGTCGTCA
N1VR1 CTGCCGGGGCGGCCTCCTGGACGACCTTCCTGAAGGCTGCCGTTCCCGCCTTCAGCCTCCAATAGGGGCGGTGCGCGACCTCATCCTCT
NpVR2 CTGCGGGGGCGGTTCCTGGATCTTCGATCTCTCCTGTGATTACTGCCGTTCCCGCCAACCTCAGCTATAGCCGCGACGCATCCTCA
N1VR2 CTGCGGGGGCGGTTCCTGGAGCTCCTCCTCCGGGATCTCGTAGTCGCGGCAACAACGATAGGGCGGGCGCGTCTACCGCTACT
T1VR1     CTGCTGCGTGGTTCGTCGTTGGTTGCCGTTTCCAGGGGTTGCCGTTCGTTGAGTCGCCTCAGTAACACGCGGACTAACACGGACGAACGAG
T1VR2     GCGGCTCCTGGAACTATCCTTGGTGTCCTCTGGCTACGACCGTCGCTGTCGCTTTAGCTCGACACCGCTGCGACGGGGCGGTCATCA
N2VR      GCGGCTCCTGGTACGACTTTCCTTGGTGGTGTCGCGCTACTATTCGTTCCGGAGGCGGTCAACG
CpVR1 CCTTTTCGTTGCGCGGGGGTTCGTGGGGCAACAAATCTGCCGTCGTCTTGTCTTGCCGGGGTCTGCAATCGGAATCGGACCTCAGGAACG
CpVR2 CCTTTTCGTTGCGCGGGGGGTTCGTGGCTCAACTTATCTGCCAATCTGTCTTGTCTTCCGATCTTCGTCAATCCGTCAGCAGGAACT
PpVR AATCTGCCCGTGCGCGTTGCGCGGCGTTCCTGGAGCAAGTATCCGACGCAAGTATCCCGACGTCTGCGTTGCTCTGCGGTACGACCTTCATCCGGCGCACAGGAGCG
```

*Figure 15 (con't)*

Figure 15 (con't)

Bordetella phage, V. harveyi, B. longum, B. thetaiotamicron, T. denticola

```
                 ?1st mismatched 'A' from 3' end of TR/VR pair
BpTR  CGAACA- TCGG GGCGCGCGGGCGTCTGTGCCATCACC TCTT  G
VhTR  ATAGCA- TCGG TTTCGCCCCGC.                TCTT  GATGT
BtTR  CAACAA- TCGG GCGTACGGGTTTGGGGTGCG         T    CCCAAGAAT
BlTR  GGAACA- TCGG GGCCGCATATCCG
TdTR  CAACAA- TCTT GGCTTCCGCTTGGCTTGTCGGCCC BpVR  CGTTCT- TCGG GGCGCGCGGCGTCTGTGACCACCTGA TCTT  GAGtag
VhVR  GTAGCA- TCGG TTTCGCCCCGCT                TCTT  TGTGtaa
BtVR  CTACTC- TCGG GCGTGCGGGTTTGGGTTGCG         T    CCCAAGAAtag
BlVR  GGCACC- TCGG GCCGCCCTTTCTGCGCGGTCGCACGAAGGCGtag
TdVR  CAGCGA- TCTT GGCTTCCGCCTGGCTTGCCGGCCTtaa
```

US 7,585,957 B2

SITE SPECIFIC SYSTEM FOR GENERATING DIVERSITY PROTEIN SEQUENCES

RELATED APPLICATIONS

This application claims benefit of priority from U.S. Provisional Patent Application Ser. No. 60/598,617, filed Aug. 3, 2004, which is hereby incorporated in its entirety as if fully set forth.

STATEMENT AS TO RIGHTS TO INVENTIONS MADE UNDER FEDERALLY SPONSORED RESEARCH AND DEVELOPMENT

This invention was made with U.S. Government support of Grant Nos. RO1 AI38417 and AI061598, both awarded by the NIH and 1999-02298, awarded by the USDA. The U.S. Government has certain rights in this invention.

FIELD OF THE INVENTION

This invention relates to the diversification of nucleic acid sequences by use of a nucleic acid molecule containing a region of sequence that acts as a template for diversification. The invention thus provides nucleic acid molecules to be diversified, those which act as the template region (TR) for directional, site-specific diversification and for encoding necessary enzymes, and methods of preparing, as well as using them.

BACKGROUND OF THE INVENTION

*Bordetella* bacteriophages generate diversity in a gene that specifies host tropism for the host bacterium. This adaptation is produced by a genetic element that combines transcription, reverse transcription and integration with site-directed, adenine-specific mutagenesis. Necessary to this process is a reverse transcriptase-mediated exchange of information between two regions, one serving as a donor template region (TR) and the other as a recipient of variable sequence information, the variable region (VR).

*Bordetella* species that cause respiratory infections in mammals, including humans, serve as hosts for a family of bacteriophages that encode a unique diversity-generating system which allows the bacteriophage to use different receptor molecules on the bacteria for attachment and subsequent infection (Liu, M. et al. Reverse transcriptase-mediated tropism switching in *Bordetella* bacteriophage. *Science* 295, 2091-2094 (2002) and Liu, M. et al. Genomic and genetic analysis of *Bordetella* bacteriophages encoding reverse transcriptase-mediated tropism-switching cassettes. *J. Bacteriol.* 186, 1503-17 (2004)). The *Bordetella* cell surface is highly variable as a result of a complex program of gene expression mediated by the BvgAS phosphorelay, which regulates the organism's infectious cycle (Ackerley, B. J., Cotter P. A., & Miller, J. F. Ectopic expression of the flagellar regulon alters development of the *Bordetella*-host interaction. *Cell* 80, 611-620 (1995); Uhl, M. A. & Miller, J. F. Integration of multiple domains in a two-component sensor protein: the *Bordetella pertussis* BvgAS phosphorelay. *EMBO J* 15, 1028-1036 (1996); Cotter, P. A. & Miller, J. F. *Bordetella*. In *Principles of Bacterial Pathogenesis*. E. Groisman, Ed. Academic Press, San Diego, Calif. pp. 619-674 (2000); and Mattoo, S., Foreman-Wykert, A. K., Cotter, P. A., Miller, J. F. Mechanisms of *Bordetella* pathogenesis. *Front Biosci* 6, E168-E186 (2001)).

Bacteriophage ("phage") BPP-1 preferentially infects virulent, Bvg+ *Bordetella* bacteria due to differential expression of phage receptor, pertactin (Prn), on the bacterial outer membrane (see FIG. 1*a* herein and Emsley, P., Charles, I. G., Fairweather, N. F., Isaacs, N. W. Structure of the *Bordetella pertussis* virulence factor P.69 pertactin. *Nature* 381, 90-92 (1996); van den Berg, B. M., Beekhuizen, H., Willems, R. J., Mooi, F. R., van Furth, R. Role of *Bordetella pertussis* virulence factors in adherence to epithelial cell lines derived from the human respiratory tract. *Infect Immun* 67, 1056-1062 (1999); and King, A. J. et al. Role of the polymorphic region 1 of the *Bordetella pertussis* protein pertactin in immunity. *Microbiology* 147, 2885-2895 (2001)). At characteristic frequencies, BPP-1 gives rise to tropic variants (BMP and BIP) that recognize distinct surface receptors and preferentially infect avirulent, Bvg– bacteria or are indiscriminate to the Bvg status, respectively. These viral parasites have thus evolved to keep pace with the dynamic surface structure displayed by their target host as it traverses its infectious cycle.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

DESCRIPTION OF THE INVENTION

The invention is based in part on the discovery that the agile tropism switching, that is switching the ability to infect specific bacteria, in *Bordetella* bacteriophages is mediated by a variability-generating cassette encoded in the phage genome (see FIG. 1*b* herein). This cassette functions to introduce nucleotide substitutions at 23 sites in a 134 bp variable region (VR) present at the 3' end of the mtd locus. Mtd, a putative tail protein, is necessary for phage morphogenesis and infectivity, and the sequence of VR within Mtd determines tropism (bacterial host) specificity. Binding of a BPP-1 derived GST-Mtd fusion protein to the *Bordetella* cell surface is dependent on expression of protein pertactin (Pm) on the outer membrane of the bacteria, correlating with the infective properties of the parental phage. The cassette shown in FIG. 1*b* therefore functions to generate plasticity in a ligand-receptor interaction via site-directed mutagenesis of, and diversification within, VR sequences.

Thus in a first aspect, the invention provides for a nucleic acid molecule comprising a variable region (VR) which is operably linked to a template region (TR) wherein said TR is a template sequence that directs site-specific mutagenesis of said VR. The nucleic acid molecule may be recombinant, in the sense that it comprises nucleic acid sequences that are not found together in nature, such as sequences that are synthetic (non-naturally occurring) and/or brought together by use of molecular biology and genetic engineering techniques from heterologous sources. Alternatively, the nucleic acid molecule may be isolated, in the sense that it comprises naturally occurring sequences isolated from the surrounding biological factors or sequences with which they are found in nature.

An operable linkage between the VR and TR regions of a nucleic acid molecule of the invention refers to the ability of the TR to serve as the template for directional, site-specific mutagenesis or diversification of the sequence in the VR. Thus in one possible embodiment of the invention, a recombinant nucleic acid molecule may comprise a donor template region (TR) and a variable region (VR) that are physically attached in cis such that the TR serves as the template sequence to direct site-specific mutagenesis in the VR. The separation between the TR and VR regions may be of any distance so long as they remain operably linked. In another embodiment, the TR and VR may not be linked in cis, but the TR retains the ability to direct site specific mutagenesis of the VR. Thus the TR and VR regions may be operably linked in trans, such that the sequences of each region are present on separate nucleic acid molecules.

The invention thus also provides for a pair of nucleic acid molecules wherein a first molecule of the pair comprises a VR which is operably linked to a TR on a second molecule of the pair. As provided by the invention, the TR is a template sequence that directs site-specific mutagenesis of said VR. The nucleic acid molecules are optionally recombinant, in the sense that they may comprise nucleic acid sequences that are not found together in nature, such as sequences that are brought together by use of molecular biology and genetic engineering techniques from heterologous sources. Of course, sequences that are brought together may be synthetic (non-naturally occurring) sequences or those that are from naturally occurring sequences but isolated from the surrounding biological factors or sequences with which they are found in nature.

In embodiments of the invention wherein the VR and TR are in trans, the TR is operably linked to sequences encoding a reverse transcriptase (RT) activity as described below. As such, the VR and reverse transcriptase encoding sequence(s) are also present in trans to each other. In some embodiments, the TR and RT activity coding sequence are in cis to each other, optionally with the TR and RT coding sequence originating from the same organism. In other embodiments, the TR and RT coding sequence may be in trans to each other while remaining operably linked so that the TR still directs RT mediated changes in the operably linked VR. Of course, the TR and/or RT coding sequence may be altered as described below relative to the naturally occurring TR in the organism. Alternatively, the TR and RT coding sequence may be heterologous to each other in that they originate from, or are isolated from, different organisms, or one or the other or both are synthetic (non-naturally occurring) or synthesized (rather than isolated). Synthetic sequences include those which are derived from naturally occurring sequences.

The invention is also based in part on the discovery that sites of variability in the VR of *Bordetella* bacteriophages correspond to adenine residues in the generally homologous template region, TR, which itself is invariant and essential for tropism switching. The invention is also based in part on the discovery that (translationally) silent (or "synonymous") substitutions in TR are transmitted to VR during switching, with TR supplying the raw sequence information for variability.

Thus the recombinant nucleic acid molecules of the invention include initial molecules wherein the TR region is identical to the VR, such that the adenine residues present in the TR will result in the mutagenesis or diversification of the corresponding positions in the VR sequence. Stated differently, the invention provides a recombinant nucleic acid molecule wherein the sequence of said TR is a perfect direct repeat of the sequence in said VR such that upon diversification of the VR region, one or more adenine residues in the VR, also found in the TR, will be mutated to another nucleotide, that is cytosine, thymine or guanine, without change in the TR sequence.

Alternatively, the invention provides recombinant nucleic acid molecules wherein the TR and VR regions are not identical such that as the TR region directs diversification of the VR. Such diversification may include the mutagenesis of nucleotide residues in the VR based upon the presence of corresponding adenine residues in the TR.

Without being bound by theory, and offered to improve the understanding of the invention, this ability may be mediated by a reverse transcription based mechanism in which a TR transcript serves as a template for reverse transcription during which the nucleotides incorporated opposite the adenine residues of the TR RNA transcript are randomized in the resulting single-stranded cDNA. The TR-derived, mutagenized cDNA sequence is then used to replace all or part of the VR in a process termed "mutagenic homing." Support for this mechanism is provided by the discovery that in *Bordetella* bacteriophages, the brt locus, which encodes a reverse transcriptase (RT), is essential for the generation of diversity. Additional support is provided by the discovery that mutagenesis occurs exclusively at sites occupied by adenines in the TR. Artificial substitution of an adenine in the TR with another nucleotide subsequently abolishes variation at that corresponding position in the VR, while introduction of an ectopic adenine subsequently produces a novel site of heterogeneity in the VR.

Thus in a further aspect, the invention provides for the diversification of VR sequences via the presence of adenine residues in the TR operably linked to the VR. The invention provides for a nucleic acid molecule wherein the TR region contains one or more adenine residues not found in the VR, such that the adenine residues present in the TR will result in the mutagenesis or diversification of the corresponding positions in the VR sequence. Stated differently, the invention provides a recombinant nucleic acid molecule wherein the sequence of said TR is an imperfect direct repeat of the sequence in said VR due to the substitution of one or more adenine residues for one or more non-adenine residues in said VR. This may be referred to as adenine-mediated diversification.

Alternatively, as compared to the VR, the TR contains one or more insertions of adenine, optionally with the insertion of additional nucleotides to maintain the correct reading frame. As a non-limiting example, groups of three nucleotides (including one or more adenines) may be inserted in-frame into the TR in order to direct the insertion of a variable codon into the VR.

In other embodiments, the invention provides for the diversification of VR sequences via the alternation of other of nucleotide residues in the TR operably linked to the VR. As a non-limiting example, the invention provides a TR that contains a deletion of one or more codons is used to direct the deletion of corresponding codons from the operably linked VR. As another example, the TR contains an insertion of one or more codons to direct the insertion of the inserted codon(s) into the operably linked VR. The TRs of the invention also include those where the TR contains a deletion or insertion of one or more nucleotides, relative to the operably linked VR, to alter the reading frame of the VR. The deletion or insertion of nucleotides in a TR to direct deletions or insertions in an operably linked VR may be used simultaneously, such as where one portion of the TR is used to direct deletion of nucleotides while another portion of the TR is used to direct insertion of nucleotides. This may be referred to as deletion/insertion mediated diversification.

In yet additional embodiments, the invention provides for diversification based upon non-adenine substitutions of residues in the TR. Thus a nucleotide in the TR may be substituted with a non-adenine residue such that the substitution is transferred to the corresponding position in the operably linked VR. As a non-limiting example, a cytosine (C) to guanine (G) substitution in a TR can be used to result in the same C to G substitution in the operably linked VR. This may be referred to as substitution-mediated diversification.

The invention also provides for the use of adenine-mediated, deletion/insertion mediated, and/or substitution-mediated diversification in any combination to alter the sequence of a VR.

In some nucleic acid molecules of the invention, an RT encoding region, and/or an atd region (or bbp7 region), in the vicinity of the 5' end of a TR may also be present. These regions may be present in cis relative to the TR region. Thus in embodiments of the invention wherein the VR and TR are in trans to each other, the atd region may be in trans relative to the VR. In other embodiments, the atd region is absent or substituted by a functionally analogous region of sequence, such as a promoter sequence that regulates or directs the expression of the TR region and operably linked RT encoding sequence.

As explained above, one property of the diversity-generating system of the invention is the directional transfer of sequence information which accompanies mutagenesis. Thus one TR is able to direct sequence changes in one or more operably linked VRs. Although a VR is highly variable, the operably linked TR is maintained as an uncorrupted source of sequence information including the information to retain the basic structural integrity of the VR encoded protein molecule. The invention is further based on the identification of a nucleic acid sequence designated IMH (initiation of mutagenic homing), which functions in determining the direction of the TR to VR transfer of sequence information.

In some embodiments of the invention, the IMH sequences are those located at the 3' end of each region in *Bordetella* bacteriophages and which comprise a 14 bp segment consisting of G and C residues followed by a 21 bp sequence. The IMH sequences at the 3' end of the VR differ at 5 positions from the sequences in the corresponding TR region (see FIG. 1c herein). The invention is also based in part on the demonstration that these polymorphisms form part of a cis-acting site that determines the directionality of homing. The demonstration was made by substituting the 21 bp VR IMH sequence with the corresponding IMH-like sequence associated with the 3' end of the TR (BPP-3'TR). The result was an elimination of tropism switching. The reverse substitution of the corresponding TR IMH-like sequence for the VR IMH sequence (BPP-3'VR) did not affect switching. Instead, the placement of VR IMH sequence at the 3' ends of both VR and TR resulted, surprisingly, in the generation of adenine-dependent variability in TR as well as in VR (see FIG. 1d herein), an event not previously observed in wild type phage. Variability continued to occur solely at positions occupied by adenine residues in the parental TR, indicating that the basic mechanism of mutagenesis was retained. Furthermore, the pattern of mutations observed in different BPP-3'VR phage indicated that TR was the sole source of both TR and VR variability (see (FIG. 1d herein).

These observations demonstrate that the sequence designated as IMH helps determine the direction of transfer of sequence information from the TR to the VR. They also support the use of the corresponding TR IMH-like sequence at the 3' end of the TR to prevent corruption of TR while the IMH directs variability to VR. Furthermore, deletion analysis indicated that in VR, the 5' boundary of information transfer is established by the extent of homology between VR and TR.

The recombinant nucleic acid molecules of the invention may thus contain an IMH sequence located at the 3' end of the VR and an IMH-like sequence at the end of the TR. Alternatively, the molecules may contain an IMH sequence at the end of both the VR and the TR such that the sequence of the TR may also vary to result in a "super-diversity" generating system.

In embodiments of the invention wherein a sequence of interest (or "desired VR") to be diversified is not operably linked to the necessary TR region, an IMH sequence can be operably located at the 3' of the desired VR followed by operable linkage to an appropriate TR with its IMH-like 3'-region. A non-limiting example of such a system is seen in the case of a desired VR which is all or part of a genomic sequence of a cell wherein insertion of an appropriate IMH and introduction of a TR containing construct with the appropriate corresponding IMH-like region, optionally with a cis linked RT coding sequence, is used to diversify the desired VR. The TR may simply be a direct repeat of the desired VR sequence to be diversified or mutagenized via the adenines present in the TR. Alternatively, the TR may contain ectopic adenines, deletions/insertions, and/or substitutions at positions corresponding to those specific sites of VR where diversity is desired. The length of homology between TR and VR can be used to functionally define the desired VR to be diversified.

The desired VR of the invention may be any nucleic acid sequence of interest for mutagenesis or diversification by use of the instant invention. In some embodiments, the sequence is all or part of a sequence encoding a binding partner of a target molecule. Target molecules may be any cellular factor or portion thereof which is of interest to a skilled person practicing the invention. Non-limiting examples include polypeptides, cell surface molecules, carbohydrates, lipids, hormones, growth or differentiation factors, cellular receptors, a ligand of a receptor, bacterial proteins or surface components, cell wall molecules, viral particles, immunity or immune tolerance factors, MHC molecules (such as Class I or II), tumor antigens found in or on tumor cells, and others as desired by a skilled practitioner and/or described herein. The binding partner (encoded at least in part by the desired VR) may be any polypeptide which, upon expression, binds to the target molecule, such as under physiological conditions or laboratory (in vivo, in vitro, or in culture) conditions.

In some embodiments of the invention, the binding partner is a bacteriocin (including a vibriocin, pyocin, or colicin), a bacteriophage protein (including a tail component that determines host specificity), capsid or surface membrane component (including those that determine physiologic, pharmacologic, or pharmaceutical properties), a ligand for a cell surface factor or an identified drug or diagnostic target molecule, or other molecules as desired and/or described herein.

Any portion, or all, of the coding region for a binding partner can be used as the desired VR. In some embodiments of the invention, however, the desired VR is the 3' portion of said sequence encoding said binding partner. The 3' portion of a coding sequence ends at the last codon. In other embodiments of the invention, the desired VR is located within about 50, about 100, about 150, about 200, about 250, about 300, or about 350 or more codons of the last codon in a coding sequence to be diversified. Stated differently, the desired VR may contain about 20, about 50, about 100, about 150, about 200, about 250, about 300, about 400, about 450, about 500, about 550, about 600, about 650, about 700, about 750, about 800, about 900, about 950, about 1000, about 1500, about 2000, about 2500, or about 3000 or more nucleotides from the last nucleotide of the coding region. In some embodiments, the IMH is not part of the translated portion of the VR, and as such may optionally be in an intron. Stated differently, some embodiments of the invention provide for an IMH which is transcribed, but not translated, or not transcribed or translated, while the VR and the larger sequence containing the VR may be transcribed and translated and encode a polypeptide.

In additional embodiments, the binding partner may be part of a fusion protein such that it is produced as a chimeric protein comprising another polypeptide. The other polypeptide member of the fusion protein may be heterologous to the binding partner. Alternatively, it may be another portion of the same binding partner such that the fusion protein is a recombinant molecule not found in nature.

In other embodiments, the desired VR for site specific mutagenesis is a non-translated, and optionally non-transcribed, regulatory region. The invention may be utilized to diversify such regulatory sequences to modify their function. In the case of 5' regulatory elements, as a non-limiting example, the invention may be used to derive regulatory regions that direct expression more strongly (e.g. a stronger promoter) or less strongly (e.g. a weaker promoter). Alternatively, the regulatory regions may be diversified to increase or decrease their sensitivity to regulation (e.g. more tightly or less tightly regulated). In the case of 3' regulatory elements, the invention may be used to derive regions that increase or decrease the stability of expressed RNA molecules. Other regulatory sequences may be similarly diversified.

As described above, the invention also provides for isolated nucleic acid molecules derived from naturally occurring sequences. Such an isolated nucleic acid molecule may be described as comprising a donor template region (TR) and a variable region (VR) wherein said TR is a template sequence operably linked to said VR to direct site specific mutagenesis of said VR. These isolated nucleic acid molecules may comprise the coding sequence containing the VR and TR as well as other components necessary to direct site specific mutagenesis of the VR in a heterologous system. Non-limiting examples of additional sequences from naturally occurring sequences are those that encode an RT activity and those that function as an IMH, to provide directionality to the transfer of sequence information from a TR to a VR, or an IMH-like sequence to prevent or reduce the frequency of changes in the TR sequence. Molecules containing these VR and TR regions with these other components are termed diversity generating retroelements (DGRs) of the invention.

These isolated nucleic acid molecules may also serve as a source of additional IMH sequences, RT coding regions, and atd regions for use in the practice of the instant invention. Non-limiting examples of isolated nucleic acid molecules include those shown in FIG. 2 herein. These include molecules isolated from *Vibrio harveyi* ML phage, *Bifidobacterium longum*, *Bacteroides thetaiotaonicron*, *Treponema denticola*, or a DGR from cyanobacteria. Non-limiting examples of such cyanobacteria include *Trichodesmium erythraeum* #1, *Trichodesmium erythraeum* #2, *Nostoc* PPC ssp. 7120 #1, *Nostoc* PPC ssp. 7120 #2, or *Nostoc punctiforme*. The relevant sequences illustrated in FIG. 2 are all publicly available and accessible to the skilled person.

In some embodiments, the invention provides an isolated nucleic acid molecule comprising a donor template region (TR) and an operably linked RT coding sequence. Such a molecule is preferably not from Bvg+ tropic phage-1 (BPP-1), Bvg− tropic phage-1 (BMP-1), or Bvg indiscriminate phage-1 (BIP-1) bacteriophage. The isolated molecule may be from a bacteriophage, a prophage of a bacterium, a bacterium, or a spirochete.

Of course, cells comprising the nucleic acid molecules of the invention are also provided. Such cells may be prokaryotic or eukaryotic, and are capable of supporting site-specific mutagenesis as described herein. Cells that are not capable of supporting such mutagenesis may still be used to replicate nucleic acid molecules of the invention or to generate their encoded protein molecules for subsequent use. In the case of eukaryotic cells, the nucleic acids of the invention may be modified for their use in a eukaryotic environment. These modifications include the use of promoter sequences recognized by a eukaryotic RNA polymerase; the introduction of intron sequences in the TR-brt to facilitate export of RNA transcripts from nucleus to cytoplasm for translation of the brt, and the presence of a nuclear localization signal (NLS) coding sequence as part of the RT coding sequence such that the RT polypeptide contains a NLS to direct its transport to, and/or retention in, the eukaryotic nucleus. In some embodiments, the NLS is located at the N or C terminus of the RT polypeptide.

In an additional aspect, the invention provides a method of site-specific mutagenesis of a nucleic acid sequence of interest present as a VR of the invention. Such a method would comprise the use of a nucleic acid molecule as described herein wherein the VR comprises said nucleic acid sequence of interest and the TR is a direct repeat of the VR or the sequence of interest. Thus, mutagenesis will be limited to the adenine residues present in the TR. Alternatively, a non-identical TR, such as a repeat of the VR or the sequence of interest containing ectopic adenine residues, insertions, deletions, or substitutions may be used. The method would further include the expression of such nucleic molecules in a cell such that one or more nucleotide positions of the VR or sequence of interest is substituted by a different residue.

Such methods of the invention may be performed to allow more than one nucleotide position of the VR or the sequence of interest to be substituted. As noted above, the VR or sequence of interest may encode all or part (such as the 3' portion) of a binding partner of a target molecule. These methods of the invention may, of course, be used to alter the binding properties of a binding partner such that its interaction with a target molecule will be changed. Non-limiting examples of such alternations include changing the specificity or binding affinity of a binding partner. The methods may be used to modify a particular binding partner such that it will bind a different target molecule. A non-limiting example of this aspect of the invention is the modification of a phage tropism determinant such that it will bind a heterologous bacterial surface component of interest. A bacteriophage that is made to express such a derivative would thus be infectious for a heterologous bacterium. This may be advantageously used as a means of creating phage or phage parts capable of binding to, infecting and/or killing (e.g. via lysis or dissipation of membrane potential) a particular strain of bacteria not normally affected by phage expressing the progenitor tropism determinant. The invention may also be used as a means of broadening or expanding the bacteriophage host range, or the binding range of a part or parts thereof, to include target molecules, species, or strains not commonly bound or infected by the parent phage or any phage. Another non-limiting example is modification of a sequence to restore or alter a binding or enzymatic activity, such as restoration of a phosphotransferase activity.

As described herein, site-specific mutagenesis of a known bacteriophage protein also may be practiced by the use of an isolated nucleic acid molecule containing a naturally occurring combination of VR and TR as described herein. Non-limiting examples of such molecules include those from *Vibrio harveyi* ML phage, *Bifidobacterium longum*, *Bacteroides thetaiotaonicron*, *Treponema denticola*, or a DGR from cyanobacteria. Non-limiting examples of such cyan bacteria include *Trichodesmium erythraeum* #1, *Trichodesmium erythraeum* #2, *Nostoc* PPC ssp. 7120 #1, *Nostoc* PPC ssp. 7120 #2, or *Nostoc punctiforme*.

In a further aspect, the invention provides a method of preparing a recombinant nucleic acid molecule as described herein by operably linking a first nucleic acid molecule comprising said VR to a second nucleic acid molecule comprising said TR such that said TR acts as a template sequence that directs site-specific mutagenesis of said VR. In the case of a linkage in cis between the VR and the TR, the first and second nucleic acid molecules would be covalently ligated together in a operative fashion as described herein. In the case of a linkage in trans, the first and second nucleic acid molecules would be placed in the same cellular environment or an in vitro reaction mix for site-specific mutagenesis in an operative fashion.

In yet another aspect, the invention provides a method of identifying additional RT coding sequences, IMH and IMH-like sequences, and corresponding TR and VR sequences. The method is based upon use of identified binding motifs of the RT activity of the invention to identify additional RT coding sequences in other organisms. The region near a putative additional RT coding sequence is then searched for nearby IMH type sequences which 1) are linked to putative TR sequences or 2) used to find VR linked IMH sequences.

The details of one or more embodiments of the invention are set forth in the accompanying drawings and the description below. Other features, objects, and advantages of the invention will be apparent from the drawings and detailed description, and from the claims.

BRIEF DESCRIPTION OF THE DRAWINGS

In FIG. 1a the specificities and tropism switching frequencies are depicted above the *B. bronchiseptica* BvgAS-mediated phase transition. BPP, BMP and BIP are tropic for Bvg+ phase, Bvg− phase or either phase, respectively. FIG. 1b (SEQ ID NO:46) shows the components of the variability-generating cassette. The 3' portion of mtd is expanded and the 134 bp VR sequence is underlined. Variable bases (red) correspond to adenine residues in TR. FIG. 1c (SEQ ID NOS:47-48) shows that in wild type (wt) BPP-1, information is transferred unidirectionally from TR to VR and is accompanied by adenine-dependent mutagenesis. BPP-3'TR fails to switch tropism, whereas BPP-3'VR switches tropism at wild type frequencies and generates variability in TR as well as VR. In FIG. 1d (SEQ ID NOS:49-59), TR adenines are shown at the top followed by the corresponding nucleotides in the parental VR. TR1-9 are TR sequences derived from in vitro variability assays performed on phage BPP-3'VR. Red nucleotides show positions that varied. Sites of variability align with adenine residues in the parental TR.

FIG. 2a shows a phylogenetic tree of DGRs in relation to other classes of retroelements. GenBank accession numbers are shown. DGR, diversity generating retroelements (red lines); G2, group II introns; Rpls, mitochondrial retroplasmids; Rtn, retrons; NLTR, non-LTR elements; LTR, LTR retroelements; Telo, telomerases; PLE, Penelope-like elements. RT domains were analyzed using the neighbor-joining algorithm of PHYLIP 3.6b, with 1000 bootstrap samplings, which are expressed as a percent. DGRs form a well-defined clade with 92% bootstrap support (red lines; Brt circled in pink). Group II introns are predicted to be their closest relatives, but with very weak support (55%). FIG. 2b shows nine putative DGRs in comparison to the *Bordetella* phage DGR. All DGRs include an ORF (191-888 aa) that contains a 103-190 bp VR (grey arrow) located at the C-terminus, a spacer region of 136-1,220 bp which in some cases contains a small open reading frame of similar size to atd, and a TR (black arrow) of equal length to VR in close proximity (22-339 bp) to RT (283-415 aa). For the *Trichodesmium* and *Nostoc* elements containing two VRs, VR1 and VR2 appear to have resulted from different mutagenic homing events originating from the same TR. E-values for RTs, in comparison to Brt, range from 1E-11 to 4E-37.

In FIG. 3a, TR of phage MS1 contains synonymous substitutions marked with black lines (see Example 1 herein); TR adenines are marked with red lines with adjacent sites represented by a single line. Data boxed in purple or blue schematically represent the VR sequences of nine independent tropism variants. Purple box, BPP-MS1-->BMP or BIP; blue box, BMP-MS1>BPP. A black line indicates that a substitution was acquired from TR; a red line indicates that a position varied with respect to the parental VR. The frequencies of transfer of synonymous substitutions (transmission histograms) are shown at the bottom. Purple bars, BPP-MS1-->BMP/BIP; blue bars, BMP-MS1-->BPP. FIG. 3b shows the results of in vitro variability assays (see Example 1 below) following selection for transfer of synonymous substitutions from TR to VR that confer resistance to MboII (position 100, boxed in purple) or AflIII (position 37, boxed in blue). Transmission histograms corresponding to the MboII selection (purple bars) or AflIII selection (blue bars) are shown at the bottom, along with positions of restriction enzyme cleavage (arrows). FIG. 3c shows that the TR of phage MS2 contains a 1 bp deletion at position 106 which, if transferred to VR, results in a frameshift mutation in mtd and non-infectious phage (see Methods). The data boxed in purple depict VR sequences of BPP-MS2-->BMP/BIP tropism variants. TR of phage MS3 contains a 1 bp deletion at position 9 which, if transferred to VR, results in non-infectious phage. The data boxed in blue show BMP-MS3-->BPP tropism variants. Transmission histograms corresponding to BPP-MS2-->BMP/BIP (purple bars) or BMP-MS3-->BPP (blue bars) reactions. Asterisks indicate the lack of transfer of frameshift mutations that are subject to negative selection.

In FIG. 4a, the average length of TR transferred under different selection conditions is shown with a histogram, and the distribution of transferred sequence lengths is depicted with bubbles (size represents the relative number of clones of a given length). Complex selections, such as those requiring a tropism switch (BPP-->BMP; BMP-->BPP), select for relatively rare isolates with longer stretches of transferred sequence. Simpler selections for transfer of single-nucleotide substitutions that result in restriction enzyme resistance (AflIIIs-->AflIIIr; MboIIs-->MboIIr) select for more abundant clones containing shorter stretches of transferred sequence, regardless of the point of selection. FIG. 4b shows the generation of VR sequences containing random portions of TR of variable length. In the model proposed with the instant invention, reverse transcription is followed by mutagenic homing, in which a TR-derived reverse transcript integrates in a homology-dependent manner at VR forming a heteroduplex. This event could initiate at the IMH site and occur by a mechanism analogous to target-primed reverse transcription (TPRT), as proposed for group II introns (Morrish, T. A. et al. DNA repair mediated by endonuclease-independent LINE-1 retrotransposition. *Nat Genet* 31, 159-165 (2002) and Wank, H., SanFilippo, J., Singh, R. N., Matsuura, M., Lambowitz, A. M. A reverse transcriptase/maturase promotes splicing by binding at its own coding segment in a group II Intron RNA. *Mol Cell* 4, 239-250

(1999)). The resulting heteroduplex would contain a high density of mismatched base pairs (red asterisks) due to adenine-specific mutagenesis. The heteroduplex is then partially converted to the parental VR sequence via mismatch repair, and/or recombination. DNA replication would produce mosaic VRs with patches of TR-derived variable sequence.

Figure 5:
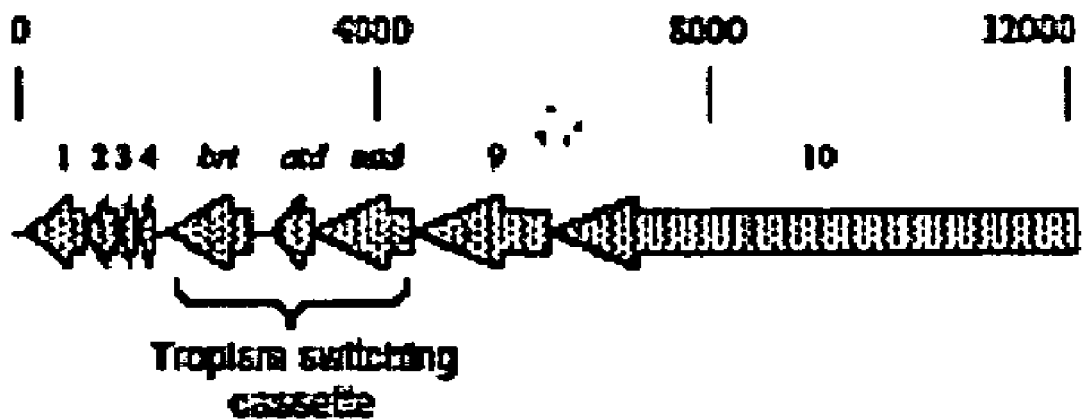
Figure 6:
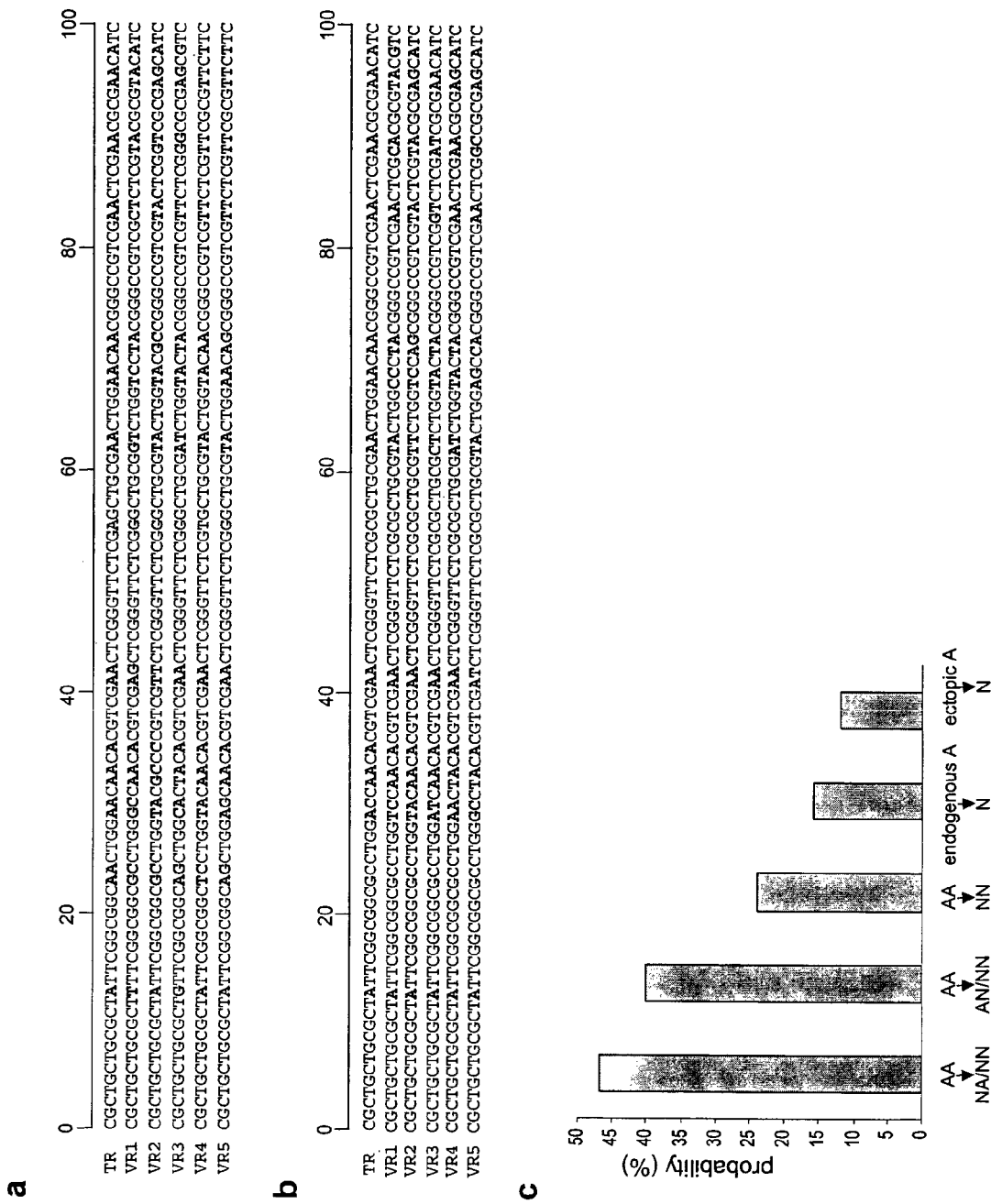
Figure 7:
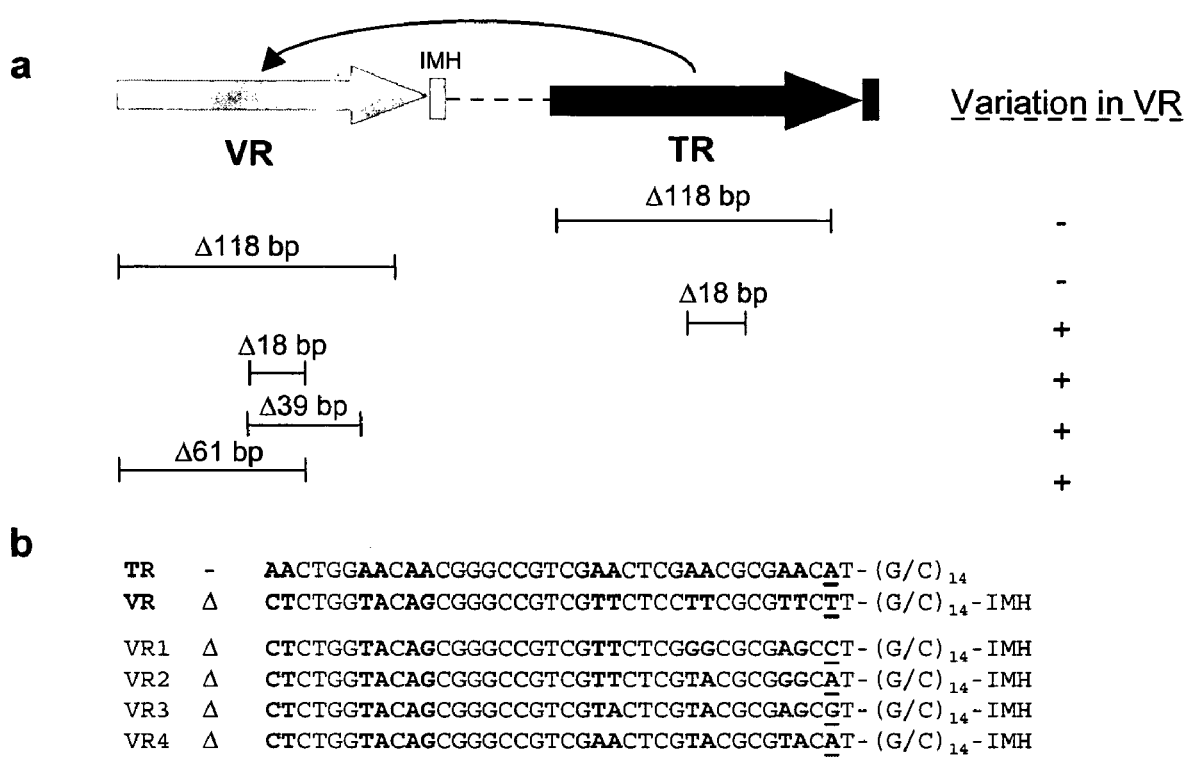

FIG. 5 shows the use of in-frame deletions to define the boundaries of the BPP-1 diversity-generating cassette. Internal in-frame deletions were introduced into phage genes flanking the brt-mtd region. A map of the BPP-1 genomic segment containing the tropism switching region is shown, along with phenotypes resulting from in-frame deletions. Viability is defined as the production of infectious phage particles following induction of lysogens with mitomycin C. Variability is defined as the production of phage DNA containing adenine mutagenized VR sequences following induction of lysogens using detected with in vitro variability assays. Phage genes bbp1, bbp2, bbp3, and bbp4 are all essential for BPP-1 viability, but unnecessary for VR variability. Phage genes brt, atd, and mtd are all necessary for VR variability in these constructions. Of these three variability cassette genes, only mtd is essential for BPP-1 viability. Phage genes bbp9 and bbp10 are not required for variability or viability. All variability determinants identified to date lie within a defined, continuous region of the phage genome, supporting the idea that the variability-generating loci function as a cassette.

FIG. 6, parts a-c, show the results of adenine-dependent mutagenesis of TR. Part a (SEQ ID NOS:60-65): the top sequence shows a TR with 23 naturally occurring adenines (bold) and an additional ectopic adenine residue introduced at a new site by site-specific mutagenesis followed by allelic exchange (position 55, red bold). VR1-VR5 show VR sequences from independently isolated tropism variants in which the ectopic adenine was observed to vary. The actual frequency of variability at the ectopic adenine is shown in part c. These data demonstrate that ectopic addition of an adenine residue in TR creates a new site of variability in VR. Part b (SEQ ID NOS:66-71): the top sequence shows a TR in which a naturally occurring adenine pair at position 23-24 has been substituted with GC (red bold). The remaining 21 naturally occurring adenines are in bold. Out of 20 independently isolated tropism variants, of which a representative 5 are shown (VR1-VR5), no variability was observed at positions 23-24. Since the frequency of alteration of the naturally occurring adenine pair at position 23-24 during tropism switching is ~95%, the elimination of adenine residues in TR eliminates variability at the corresponding position in VR. Part c: frequencies of mutagenesis at transmitted adenines were calculated using in vitro variability assays. The frequency of mutagenesis at pairs of transmitted adenines resulting in a substitution at either position (AA->NA/NN; AA->AN/NN) or both positions (AA->NN) is shown (n=20). Mutagenesis frequencies at the single endogenous adenine at position 35 (endogenous A->N, n=50) or the ectopic adenine at position 55 (ectopic A->N, n=50) are also shown. As observed and provided within the scope of the invention, an adenine that is part of a pair is much more likely to vary than a single adenine, and the frequency of variability at the ectopic adenine at position 55 (see Part a above) is nearly identical to that for the endogenous adenine at position 35.

FIG. 7, parts a and b, show the results of internal deletion experiments. Part a: stretches of sequence were deleted from TR and VR of BPP-1 as indicated on the diagram (to scale) and the resulting strains were tested for variation in VR using in vitro variability assays. Variation in VR is indicated by "+" in the column to the right, while lack of variation is indicated by a "–". Except for very large deletions (D118), the system was able to accommodate deletions of different size and location (Δ18, Δ39, Δ61). Most significantly, a large deletion of the 5' portion of VR (Δ61) still displayed variation, indicating that there is no 5' cis-acting site analogous to IMH and that homing in this system is in part based on homology. Part b: sequences of variant VRs (VR1-4) derived from Δ61 phage are aligned against TR and VR (above) (SEQ ID NOS:72-77). The sequence between the deletion and the G/C stretch is shown. The MboII site of selection is also shown (underlined), together with mutagenesis (red) at residues corresponding to adenines in TR (bold).

FIG. 8, parts a and b, show the tropism switching frequencies of phage carrying multiple substitutions in TR. Strain abbreviations are the same as in FIG. 3. MS 1 carries 5 synonymous substitutions while MS2 and MS3 carry a 1 bp deletion in addition to synonymous substitutions (see maps in FIG. 3). Part a: multiple substitution constructs in the BMP-1 background (MS1, MS2, MS3) or wild type BMP-1 were selected for switching to the BPP tropism. Phage induced from lysogens were propagated on Bvg$^-$ bacteria and the fraction of phage able to form plaques on Bvg+ was measured. Part b: multiple substitution constructs in the BPP-1 background or wild type BPP-1 were selected for switching to the BMP or BIP tropisms. Phage induced from lysogens were propagated on a Bvg+ host and the fraction of phage able to form plaques on a Bvg$^-$ host was measured. In parts a. and b, the frequencies of tropism switching for MS2 and MS3 phages are lower than wild-type, indicating that a fraction of phage was eliminated by negative selection. In both cases, however, these mutant phages were able to switch tropism while avoiding the transmission of frameshift mutations (FIG. 3*c*).

FIG. 9 shows the nucleotide sequence alignments of VRs and TRs from different DGRs (SEQ ID NOS:78-100). TR sequence is shown on top with VR sequence(s) on the bottom. Stop codons are shown in lower case. Adenines in TR are shown in bold, while the corresponding bases in VR are boldfaced only if different from TR. Note that the differences are largely limited to TR adenines, as opposed to non-adenine substitutions, indicating that the basic mechanism of mutagenesis is conserved across DGRs. Mismatches at the 3' end, similar to IMH in *Bordetella* phage, are shown in color (green, VR; blue, TR). In addition, a well-conserved TCTT motif at the 3' end, whose functional significance is unclear, is underlined. These similarities attest to likely conservation of mechanistic features, despite the lack of sequence identity between the different elements.

FIG. 10 shows schematics representing constructs of the invention. In the first construct, an atd region is present between the 3' end of the indicated terminator and the start of the TR region. In the second construct, the atd region is present between the promoter and the indicated TR region. In the third construct, no atd or TR region is present in the construct.

FIG. 11 shows mutagenesis of VR on an induced prophage.

FIG. 12 shows an illustration of the design to mutagenize a heterologous sequence with a novel TR and IMH.

FIG. 13 shows an illustration of constructs used to mutagenize a phosphotransferase encoding sequence.

FIG. 14 (SEQ ID NOS:101-103) shows the VR amino acid sequence used in the mutagenesis of a non-*Bordetella* APH (3')-IIa encoding sequence. The large "L" delineates the location of the insertion of an amber codon at position 243 for the elimination of kanamycin binding and inactivation of kanamycin resistance.

Figure 15:
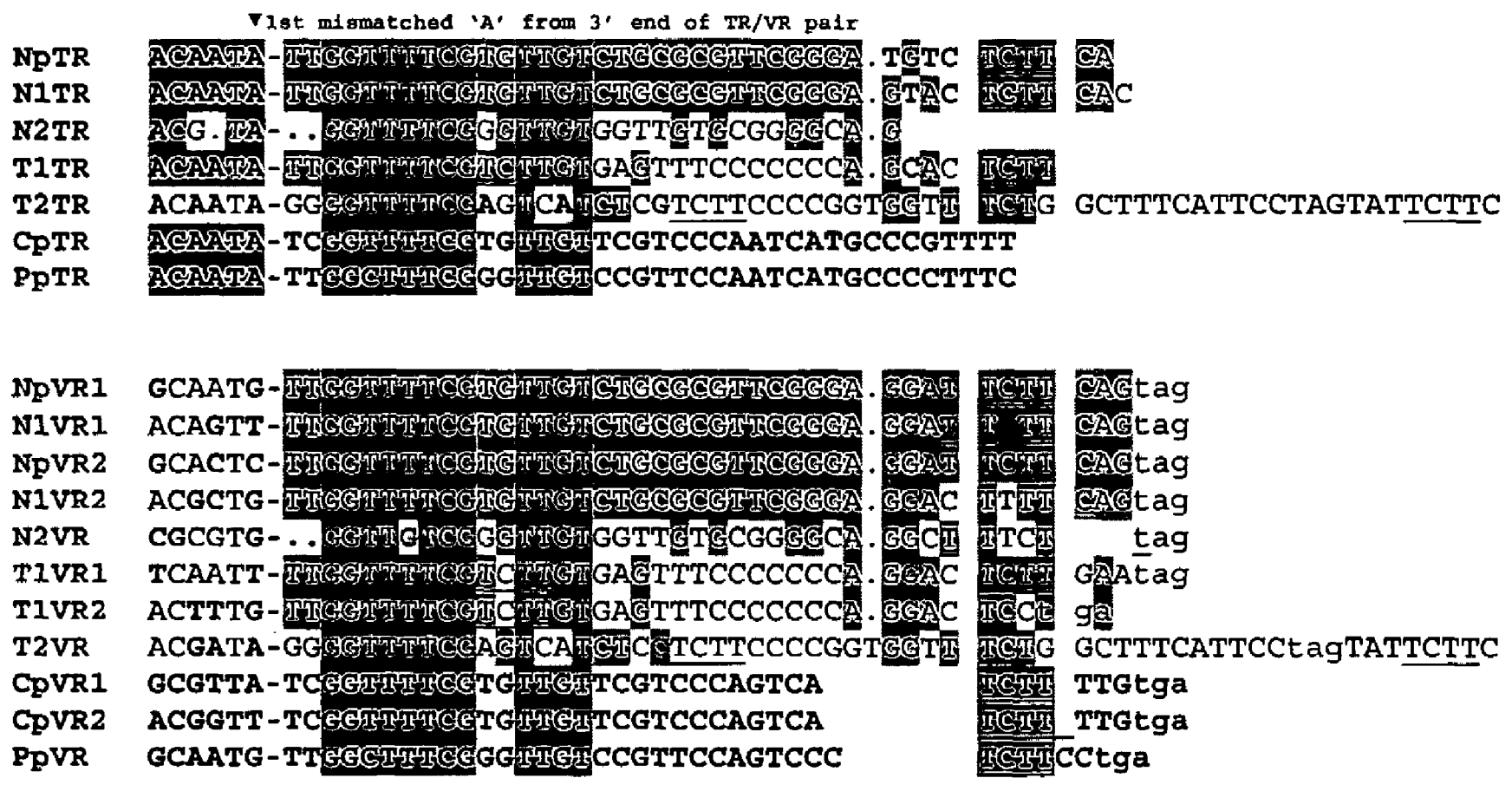

FIG. 15 shows an alignment of sequences (SEQ ID NOS: 98, 93, 96, 88, 91, 24, 27, 99, 94, 100, 95, 97, 89, 90, 92, 25, 26, 28, 1, 7, 5, 3, 9, 2, 8, 6, 4, 10) from various DGRs (including Cyanobacterial DGRs, and those from *Nostoc punctiforme*, *Nostoc* spp. 7120 #1 & #2, *Trichodesmium Erythraeum* #1 & 42 and others) of the invention.

DETAILED DESCRIPTION OF SPECIFIC MODES OF PRACTICING THE INVENTION

This invention provides nucleic acid molecules and methods for their use in site specific mutagenesis of a sequence of interest which is in whole or in part the VR in a operative linkage between the VR and a homologous repeat (TR) that directs the diversification of the sequence of interest at positions occupied by adenines within the TR. The extent of diversity that can be generated by the invention is not equal to the number of adenine positions that are capable of directing substitutions in the VR. Instead, each adenine in TR can result at that position in 3 different nucleotide substitutions in the VR, many of which will result in a substituted amino acid at the corresponding position encoded by the VR. As a non-limiting example, the presence of 23 adenine nucleotides in the practice of the invention is theoretically capable of generating over $10^{12}$ distinct polypeptide sequences.

Thus the invention provides for the presence of up to 23 or more adenine nucleotides in a given TR of the invention to direct mutagenesis in the corresponding VR. The presence of adenine residues may be due to natural occurrence in the TR or the result of deliberate insertion or substitution into the TR as described herein. In the case of naturally occurring adenine nucleotides in the TR, mutagenesis may be allowed to occur or may be avoided by a substitution of the adenine nucleotide to a non-adenine nucleotide without changing the encoded amino acid (silent substitution). In the case of deliberate insertion or substitution, the invention provides for the introduction of 1, 2, 3, 4, 5, 6, 7, 8, 9, 10, 11, 12, 13, 14, 15, 16, 17, 18, 19, 20 or more adenine nucleotides into a TR.

As described herein, the invention provides recombinant and isolated nucleic acid molecules comprising a variable region (VR) which is operable linked to a template region (TR), wherein the VR and TR sequences are in the same molecule or separate molecules, and wherein said TR is a template sequence operably linked to said VR in order to direct site specific mutagenesis of said VR. Preferably, however, the molecule is not a derivative, containing only one or more deletion mutations, of the major tropism determinant (mtd) gene, the atd region, and/or the brt coding sequence, of Bvg+ tropic phage-1 (BPP-1) bacteriophage.

The VR and TR regions may be physically and operably linked in cis or operably linked in trans as described herein. The separation between the two regions when linked in cis can range from about 100 base pairs or less to about 1200 base pairs or more. When associated via a cis or trans configuration, expression of the TR and operably linked RT coding sequence may be under the control of an endogenous or heterologous promoters. When associated in trans, expression of the TR and operably linked RT coding sequences may be under the control of an endogenous or heterologous, regulatable promoter or promoters.

The nucleic acid molecules of the invention may also contain an RT encoding region in cis with the TR region. Non-limiting examples of RT coding sequences include those from *Vibrio harveyi* ML phage, *Bifidobacterium longum*, *Bacteroides thetaiotaonicron*, *Treponema denticola*, or a DGR from cyanobacteria, such as *Trichodesmium erythrism*, the genus *Nostoc*, or *Nostoc punctiforme* as provided herein. The relevant RT encoding sequences from these sources are all publicly accessible and available to the skilled person. Additionally, some nucleic acid molecules may contain an atd region (or bbp7 region) immediately 5' of the TR. Without being bound by theory, and offered to improve the understanding of the invention, the atd region is believed to participate in regulating transcription of the TR and so may be augmented by use of a heterologous promoter.

In embodiments of the invention comprising the use of a heterologous promoter, the promoter may be any that is suitable for expressing the TR and RT coding sequence under the conditions used. As a non-limiting example, when a prokaryotic cell is used with the VR and TR regions, the promoter may be any that is suitable for use in the prokaryotic cell. Non-limiting examples include the filamentous haemagglutinin promoter (fhaP), lac promoter, tac promoter, trc promoter, phoA promoter, lacUV5 promoter, and the araBAD promoter. When the conditions are those of a eukaryotic cell, non-limiting examples of promoters include the cytomegalovirus (CMV) promoter, human elongation factor-1E promoter, human ubiquitin C (UbC) promoter, SV40 early promoter; and for yeast, Gal 11 promoter and Gal 1 promoter. Of course, the VR may remain under the control of an endogenous promoter, if present, or be under the control of another heterologous promoter independently selected from those listed above or others depending on whether a prokaryotic or eukaryotic cell is used. If a cell-free system is used in the practice of the invention, then the promoter(s) will be selected based upon the source of the cellular transcription components, such as RNA polymerase, that are used.

The nucleic acid molecules of the invention may also contain an IMH sequence or a functional analog thereof. The function of the IMH has been described above, and the invention further provides for the identification, isolation, and use of additional functionally analogous sequences, whether naturally occurring or synthetic. In the case of naturally occurring functional analogs, they may be used with heterologous VR and TR sequences in the practice of the instant invention.

Non-limiting examples of IMH and IMH-like sequences for use in the practice of the invention include those shown in the following Table. An IMH or IMH-like sequence may contain the GC-rich region through the 3' end.

TABLE 1

| VR 3'-end | GC-rich region (50-91% GC); length (4-31 nt) TC or TTGG . . . start nucleotide runs (3-7 nt) | mismatches (1-5) length (1-9 nt) | IHM 3' end |
|---|---|---|---|
| BPP1 | | | |
| TR GCGAACA- | TCGG-GGCGCGCGGCGTCTGTG (81% GC) | CCCATCACC | TTCTTG (SEQ ID NO:1) |

TABLE 1-continued

| VR 3'-end | GC-rich region (50-91% GC); length (4-31 nt) TC or TTGG . . . start nucleotide runs (3-7 nt) | mismatches (1-5) length (1-9 nt) | IHM 3' end |
|---|---|---|---|
| VR GCGTTCT- | TCGG-GGCGCGCGGCGTCTGTG (21 nt) | ACCACCTGA | TTCTTGAGtag (SEQ ID NO:2) |
| *B. Longum* | | | |
| TR TGGAACA- | TCGG-GGGCCGC (91% GC) | ATATCC | G (SEQ ID NO:3) |
| VR TGGCACC- | TCGG-GGGCCGC (11 nt) | CTTTCT | GCGCTCGGTCGCACGAAGGCGtag (SEQ ID NO:4) |
| *Bacteriodes T.* | | | |
| TR ACAACAA- | TCGG-GCGTACGGGTTTGGG (68% GC) | G | TGCGTTCTTCCCAAGAAT (SEQ ID NO:5) |
| VR ACTACTC- | TCGG-GCGTGCGGGTTTGGG (19 nt) | T | TGCGTTCTTCCCAAGAAtag (SEQ ID NO:6) |
| *Vibrio Harveyi* | | | |
| TR AATAGCA- | TCGG-TTTTCGCCCCGCT (65% GC) | CTTGA | TGT (SEQ ID NO:7) |
| VR AGTAGCA- | TCGG-TTTTCGCCCCGCT (17 nt) | TTCTT | TGTGtaa (SEQ ID NO:8) |
| *T. denticola* | | | |
| TR GACAACAA- | TCTT-GGCTTCCGCTTGGCTTG (57% GC) | TCGGCCC | (SEQ ID NO:9) |
| VR TGCAGCGA- | TCTT-GGCTTCCGCCTGGCTTG (21 nt) | CCGGCCT | taa (SEQ ID NO:10) |
| *Trichodesmium Erythraeum #2* | | | |
| TR CGAGTCA- | TCTCGTCTTCCCCGGTGGTTTCTGGCTTTCATTCCTAGTATTCTTC | (SEQ ID NO:11) | |
| VR CGAGTCA- | TCTCCTCTTCCCCGGTGGTTTCTGGCTTTCATTCCtagTATTCTTC | (SEQ ID NO:12) | |
| *Trichodesmium Erythraeum #1* | | | |
| TR CAACAATA- | TTGGTTTTCGT-CTTGT-GAGTTTCCCCCCCAG (52% GC) | C | ACTCTT (SEQ ID NO:13) |
| VR1 CATCAATT- | TTGGTTTTCGT-CTTGT-GAGTTTCCCCCCCAG (31 nt) | G | ACTCTTGAAtag (SEQ ID NO:14) |
| VR2 CGACTTTG- | TTGGTTTTCGT-CTTGT-GAGTTTCCCCCCCAG | G | ACTCCtga (SEQ ID NO:15) |
| *Nostoc spp. 7120 #1* | | | |
| TR AACAATA- | TTGGTTTTCGT-GTTGT-CTGCGCGTTCGGGAG (55% GC) | TACTC | TTCAC (SEQ ID NO:16) |
| VR1 TACAGTT- | TTGGTTTTCGT-GTTGT-CTGCGCGTTCGGGAG (31 nt) | GATTC | TTCAGtag (SEQ ID NO:17) |
| VR2 TACGCTG- | TTGGTTTTCGT-GTTGT-CTGCGCGTTCGGGAG | GACTT | TTCAGtag (SEQ ID NO:18) |
| *Nostoc Punctiforme* | | | |
| TR AACAATA- | TTGGTTTTCGT-GTTGT-CTGCGCGTTCGGGA (53% GC) | TGTC | TCTTCA (SEQ ID NO:19) |
| VR1 AGCAATG- | TTGGTTTTCGT-GTTGT-CTGCGCGTTCGGGA (30 nt) | GGAT | TCTTCAGtag (SEQ ID NO:20) |
| VR2 AGCACTC- | TTGGTTTTCGT-GTTGT-CTGCGCGTTCGGGA | GGAT | TCTTCAGtag (SEQ ID NO:21) |
| *Nostoc spp.* | | | |

TABLE 1-continued

| VR 3'-end | GC-rich region (50-91% GC); length (4-31 nt) TC or TTGG . . . start nucleotide runs (3-7 nt) | mismatches (1-5) length (1-9 nt) | IHM 3' end |
|---|---|---|---|
| *7120 #2* | | | |
| TR CAACGTA- | --GGTTTTCGG-GTTGT-GGTTGTGCGGGGCA | G | (SEQ ID NO:22) |
| VR GCGCGTG- | --GGTTGTCGG-GTTGT-GGTTGTGCGGGGCA | GGCT | TTCTtag (SEQ ID NO:23) |
| *Chlorobium phaeobacteroides* | | | |
| TR AACAATA- | -TCGG-TTTTCGT-GTTGT-TCGTCCCA | ATCA | TGCCCGTTTTATGGTGCGGTAA (SEQ ID NO:24) |
| VR1 GGCGTTA- | -TCGG-TTTTCGT-GTTGT-TCGTCCCA | GTCA | TCTTTTGtgaTTATCTGAT (SEQ ID NO:25) |
| VR2 TACGGTT- | -TCGG-TTTTCGT-GTTGT-TCGTCCCA | GTCA | TCTTTTGtgaTTATCTGATAC (SEQ ID NO:26) |
| *Pelodictyon phaeoclathratiforme* | | | |
| TR AACAATA- | -TTGG-CTTTCGG-GTTGT-CCGTTCCA | ATCAT | GCCCCTTTCGATGCGTGTTAAAG (SEQ ID NO:27) |
| VR GGCAATG- | -TTGG-CTTTCGG-GTTGT-CCGTTCCA | GTCCC | TCTTCCtgaTCTTCTGTCTTTCT (SEQ ID NO:28) |
| *Prosthecochloris aestuarii* | | | |
| TR ACAACAA- | TTTGGGCTTCCGG-GTTGT-GAG | TACAAAG | TATCGCCAGATGGGGATTGTTTAC (SEQ ID NO:29) |
| VR1 ACGACGT- | TTTGGGCTTCCGC-CTTGT-GAG | GCAGCCT | tagTATCCCTTGGGGTTT (SEQ ID NO:30) |
| VR2 ACGACGA- | TTTGGGCTTCCGC-CTTGT-GAG | GCAGCCT | tagTATCTCTTGGGGTTTTTACCA (SEQ ID NO:31) |

In yet another aspect, the invention provides a method of identifying additional RT coding sequences, IMH and IMH-like sequences, TR sequences, and VR sequences. In one embodiment, the invention provides a method of identifying relevant RT coding sequences by searching sequences for the presence of one or both of a conserved nucleotide binding site motif including amino acid sequences IGXXXSQ (SEQ ID NO:32) or LGXXXSQ (SEQ ID NO:33), where "X" represents any naturally occurring amino acid. Any suitable methodology for searching sequence information may be used. Non-limiting examples include the searching of protein sequence databases with BLAST or PSI-BLAST.

The invention also provides a method of identifying IMH sequences, said method comprising identifying an RT coding sequence in a genome of an organism, optionally as described above, search the coding strand within about 5 kb of the RT ORF and identify an IMH-like sequence containing an 18-48 nucleotide stretch of adenine-depleted DNA; and a) use the putative IMH-like sequence to search genome-wide for a closely-related putative IMH and compare the DNA sequences located 5' to the IMH-like and putative IMH sequences to find homologous TR and VR regions, respectively; or b) use the sequence of the DNA located 100-350 base-pairs long 5' to the IMH-like sequence to identify a putative TR, and use all or parts of this TR and IMH-like sequence to search genome-wide for a matching putative VR and IMH sequence.

A potential VR region may be optionally selected for further analysis if present within coding sequence(s) or putative coding sequence(s). A potential TR may be optionally selected based on location in an intergenic region near the RT coding sequence. Of course sequence alignments of potential TR and VR regions may also be used to confirm their operative linkage, especially if sequence differences occur mainly at adenines. As a non-limiting example, the sequences may be more than about 80%, more than about 85%, more than about 90%, or more than about 95% homologous, with the majority of differences being at the locations of the adenines bases in the TR. As an additional option, the identification of the TR or VR sequences may include searching or identification of sequences that are about 100 to about 350 base-pairs long or longer.

With respect to identifying the IMH-like, or IMH, sequence, searching for a conserved sequence selected from TCGG, TTTTCG, or TTGT at the 3' ends of possible TR and VR regions may be used. FIG. 9 shows some conserved sequence patterns following the 3'-most nucleotides that vary between TR and VR pairs.

Conserved sequence patterns have been identified as following the 3'-most nucleotides that vary between TR and VR pairs. Comparison of the regions following the VR region (up to or slightly past the position of the VR-containing genes stop codons) revealed several common features, including 1) the length of the regions range from about 18 to about 44 nucleotides (average length of about 38); 2) regions had no or few adenine nucleotides; 3) nearly all (19/23) begin with a TC or TT followed by a sub-region rich in mono- and di-nucleotide runs; 4) all have one or more mismatches near the 3' end (up to 5 mismatches in a 9 nucleotide stretch); and 5) the majority (13/23) have a TCTT motif and others (5/23) a similar motif near the 3' end of the region. Thus IMH and IMH-like sequences of the invention may be designed to possess one or more of these features.

The above methods may be in the form of a bioinformatic algorithm to identify DGRs and IMHs. As would be recognized by the skilled person, the above methods may be embodied in the form of a computer readable medium (such as software).

As one alternative, the BPP1 brt protein sequence may be used to search for homologs in the protein database using PSI-BLAST. Brt homologs from previously identified, putative DGRs may be used for a second iteration search, and top hits may be examined further for TR and IMH-like sequences in the vicinity of the RT coding sequence. In some embodiments, genomic regions of about 2000 to 5000 bp upstream and downstream from the RT coding sequence in the genomes of organisms with closely related RT genes may be searched for direct repeats, such as for ≦ repeats of >50 nt long. Potential TR and VR regions may be identified if repeats occurred at the 3'-end of an upstream gene and in the intergenic region upstream of the RT gene. Sequence alignment of putative TR and VR regions identified putative DGRs if sequence differences occurred mainly at adenines. The 3' ends of the putative TR and VR regions may be examined for conserved IMH and IMH-like sequence motifs as described above.

The invention further provides at least two pattern classes derived from alignments of the non-varying 3' ends of TRs and VRs. Cyanobacterial sequences form a highly similar sub-group, while other TR/VR pairs have conserved sequence motifs at one or both the ends of the regions with dissimilar internal sequences (see FIG. 15). Stop codons were located at variable distances downstream from conserved sequence motifs in each region.

Non-limiting examples of sequences for site-specific mutagenesis according to the invention are those encoding all or part of a binding partner of a target molecule. Non-limiting examples of binding partners include amylin, THF-γ2, adrenomedullin, insulin, VEGF, PDGF, echistatin, human growth hormone, MMP, fibronectin, integrins, calmodulin, selectins, HBV proteins, HBV antigens, HBV core antigens, tryptases, proteases, mast cell protease, Src, Lyn, cyclin D, cyclin D kinase (Cdk), p16$^{INK4}$, SH2/SH3 domains, SH3 antagonists, ras effector domain, farnesyl transferase, p21$^{WAF1}$, Mdm2, vinculin, components of complement, C3b, C4 binding protein (C4BP), receptors, urokinase receptor, tumor necrosis factor (TNF), TNFα receptor, antibodies (Ab) and monoclonal antibodies (MAb), CTLA4 MAb, interleukins, IL-1, IL-2, IL-3, IL-4, IL-5, IL-6, IL-7, IL-8, IL-9, IL-10, IL-11, IL-12, IL-13, IL-17, interferons, LIF, OSM, CNTF, GCSF, interleukin receptors, IL-1 receptor, c-MpI, erythropoietin (EPO), the EPO receptor, T cell receptor, CD4 receptor, B cell receptor, CD30-L, CD40L, CD27L, leptin, CTLA-4, PF-4, SDF-1, M-CSF, FGF, EGF.

In some embodiments of the invention, the binding partner is a bacteriocin (including a vibriocin, pyocin, or colicin), a bacteriophage protein (including a tail component that determines host specificity), capsid or surface membrane component, a ligand for a cell surface factor or an identified drug or diagnostic target molecule.

In additional embodiments, the binding partner may be part of a fusion protein such that it is produced as a chimeric protein comprising another polypeptide. The other polypeptide member of the fusion protein may be selected from the following non-limiting list: bacteriophage tail fibers, toxins, neurotoxins, antibodies, growth factors, chemokines, cytokines, neural growth factors.

In additional embodiments, the binding partner may be a nucleic acid, part of a nucleic acid molecule, or an aptamer.

As described above, the invention also provides for isolated nucleic acid molecules derived from naturally occurring sequences. Such an isolated nucleic acid molecule may be described as comprising a donor template region (TR) and a variable region (VR) wherein said TR is a template sequence operably linked to said VR in order to direct site specific mutagenesis of said VR. Preferably, the molecule is from a bacteriophage but not from Bvg+ tropic phage-1 (BPP-1), Bvg⁻ tropic phage-1 (BMP-1), or Bvg indiscriminate phage-1.

The nucleic acid molecules of the invention may be part of a vector or a pair of vectors that is/are introduced into cells that permit site-specific mutagenesis of the VR and/or support replication of the molecules. Non-limiting examples of vectors include plasmids and virus based vectors, including vectors for phage display that may be used to express a diversified VR sequence. Other non-limiting embodiments are vectors containing VR sequences that have been subjected to the methods of the instant invention and then removed from an operably linked TR, including by preventing the expression of TR, so as to produce without further diversification quantities of the VR-encoded protein for uses including as a diagnostic, prognostic, or therapeutic product.

The instant invention also provides for a "diversified collection" of more than one VR sequence, per se or in the context of a vector, wherein at least two of the VR sequences differ from each other in sequence. In some embodiments, the difference in sequence results in the encoding of a different polypeptide by the VR sequence, but the difference may also be silent or synonymous (different codon encoding the same amino acid) and optionally used in cases where codon optimization is needed to improve expression of the encoded polypeptide. A "diverse collection" may also be referred to as a library or a plurality of VR sequences, per se or in the context of a vector. Thus the invention also provides a plurality or library of nucleic acid molecules as described herein. The plurality or library of molecules may include those wherein the VR has undergone diversification directed by the operably linked TR.

Non-limiting examples of cells that contain the nucleic acids of the invention include bacterial cells that support site-specific mutagenesis of bacteriophages as described herein or eukaryotic cells of any species origin that support mutagenesis and/or production and processing of recombinant mutagenized protein. In some embodiments, yeast or fungal cells may be used. In other embodiments, higher eukaryotic cells may be used.

Having now generally described the invention, the same will be more readily understood through reference to the following examples which are provided by way of illustration, and are not intended to be limiting of the present invention, unless specified.

EXAMPLES

Example 1

Materials and Methods

Bacterial Strains, Phase and Plasmids.

*B. bronchiseptica* strains were derived from the sequenced RB50 strain (Uhl et al. and Parkhill, J. et al. Comparative analysis of the genome sequences of *Bordetella pertussis, Bordetella parapertussis* and *Bordetella bronchiseptica. Nat Genet* 35, 32-40 (2003)) and BPP-1 was induced from a rabbit isolate of *B. bronchiseptica* (Liu et al. 2002). BMP-1 was isolated from BPP-1 using the tropism switch assay (see below). Plate lysates were prepared using the soft-agar overlay method (Adams, M. H. *Bacteriophages*. (Interscience Publishers Inc, New York, N.Y., 1959) and tropism switch assays were performed as described previously (Liu et al. 2002). Bacterial and phage constructs were generated using allelic exchange (Edwards, R. A., Keller, L. H., Schifferli, D. M. Improved allelic exchange vectors and their use to analyze 987P fimbria gene expression. *Gene* 207, 149-157 (1998) and Figurski, D. H. & Helinski, D. R. Replication of an origin-containing derivative of plasmid RK2 dependent on a plasmid function provided in trans. *Proc Natl Acad Sci USA* 76, 1648-1652 (1979).

Multiple Substitution Constructs.

BPP-MS1 and BMP-MS1 (FIGS. 3*a* and 3*b*) are BPP-1 and BMP-1 derivatives, respectively, containing the following synonymous substitutions in TR: T7-A (PstI), G37-T (BstXI), C55-A (XhoI), C79-G (ApaI) and G100-C (NlaIII). Each substitution generates a unique restriction site as indicated. The substitutions at positions 37 and 100 eliminate AflIII and MboII restriction sites, respectively, allowing in vitro selections for variability (FIG. 3*b*). Phage MS2 (FIG. 3*c*) is a Bpp-1 derivative containing a 1 bp deletion at position 106 in TR and substitutions: T7-A, G37-T, C55-A, C-79G. Phage MS3 (FIG. 2*c*) is a BMP-1 derivative containing a 1 bp deletion at position 9 in TR and substitutions: G37-T, C-55A, C79-G and G100-C.

In Vitro Variability Assays.

In vitro variability assays select for transfer, from TR to VR, of single nucleotide substitutions that confer resistance to restriction enzyme cleavage. Lysogens were induced with mitomycin C and VR sequences were amplified by PCR and digested with the appropriate restriction enzymes. The amplification-restriction cycle was repeated with nested primers until no further cutting was observed and the products were cloned into pBluescript KS+ vector (Stratagene) for sequencing. Variability in TR due to "self-homing" (FIG. 1*c*, BPP-3'VR) was assayed using BsrI, which cleaves the parental TR but not TR sequences with adenine modifications that confer resistance. For the multiple substitution experiments in FIG. 3*b*, amplification products were purified and digested with AflIII for BMP-MS1 phage or MboII for BPP-MS1 phage. In both cases, parental VR sequences are subject to cleavage whereas phage in which specific synonymous substitutions that eliminate restriction enzyme cleavage sites are transferred from TR are resistant.

Bioinformatics.

Annotated BPP-1 sequence is available under GenBank accession number AY029185. Database entries containing the conserved reverse transcriptase catalytic domain (Pfam 00078 rvt) were compiled and phylogenetic profiles were constructed using PHYLIP software package (at evolution.genetics.washington.edu/phylip.html). Entries that grouped together with Brt were searched for the presence of direct repeats proximal to the RT using REPuter program (Kurtz, S. et al. REPuter: the manifold applications of repeat analysis on a genomic scale *Nucleic Acids Res*. 29, 4633-2642 (2001)). Artemis software was used to collect data and facilitate annotation (Rutherford, K. et al. Artemis: sequence visualization and annotation. *Bioinformatics* 16:944-945 (2000)).

Example 2

Multiple Synonymous Substitutions

A genetic strategy for tracking events that give rise to sequence variants was designed based on the observation that conservative nucleotide substitutions in TR are incorporated into VRs of phages that have switched tropism. By introducing multiple synonymous substitutions positioned along TR, the portion of TR transferred during a switching event can be determined by recording the pattern of substitutions appearing in VR. Mechanistic events that underlie tropism switching can then be reconstructed from the resulting "haplotype" profiles.

Information was observed as not being transmitted evenly across VR. FIG. 3*a* shows the patterns of transmission accompanying BPP-->BMP/BIP or BMP-->BPP tropism switching. In both cases, 3' markers were transmitted with 100% efficiency whereas 5' markers were transmitted at frequencies approaching 50%. Variability at adenines correlated with the transfer of proximal substitutions, while lack of variability correlated with their absence. In several cases, mosaic patterns were observed in which stretches of variable, TR-derived sequence were interrupted by non-variant, VR-derived sequence (bullets, FIG. 3*a*). Together, these results argue against a simple cut and paste mechanism as commonly observed in transposition reactions (Pena, C. E., Kahlenberg, J. M., Hatfull, G. E. Assembly and activation of site-specific recombination complexes. *PNAS* 97, 7760-5 (2000) and Hallett B., Sherratt, D. J. Transposition and site-specific integration: adapting DNA cut-and paste mechanisms to a variety of genetic rearrangements. *FEMS Microbiol Rev* 21, 157-78).

Because the sequence determinants that govern receptor specificity are unclear, tropism switching assays are inherently biased by a powerful, yet poorly defined, set of selective pressures. Substitution patterns were therefore recorded using PCR-based in vitro assays that select for variability at single, precisely defined positions, with no selection for tropism switching or phage infectivity. These assays are based on the loss of restriction sites in parental VR sequences that result from the transmission of synonymous substitutions in TR.

As shown in FIG. 3*b*, in vitro variability assays revealed selection-specific patterns of marker transfer in which AflIII-selected clones preferentially transferred the middle portion of TR containing the selected site (position 37), and transfer frequencies precipitously fell in either direction. MboII-selected clones transferred the 3' end of TR which contains the selected site (position 100), but were indifferent to sequence variation at the 5' end. In both cases, maximal frequencies of marker transfer were shifted to the exact point of selection. The majority of events displayed either interrupted patterns of transmission or patches of transmission flanked by invariant sequence (bullets, FIG. 3*b*).

Despite the lack of selection for mutagenesis, all of the VR sequences in FIG. 3*b* contain adenine-substitutions. To further probe the extent of plasticity, a strong negative selection against transfer of the 3' or 5' boundaries of TR was imposed. This was accomplished by the introduction of frameshift mutations which, if transferred, produce non-viable phage.

Figure 1:
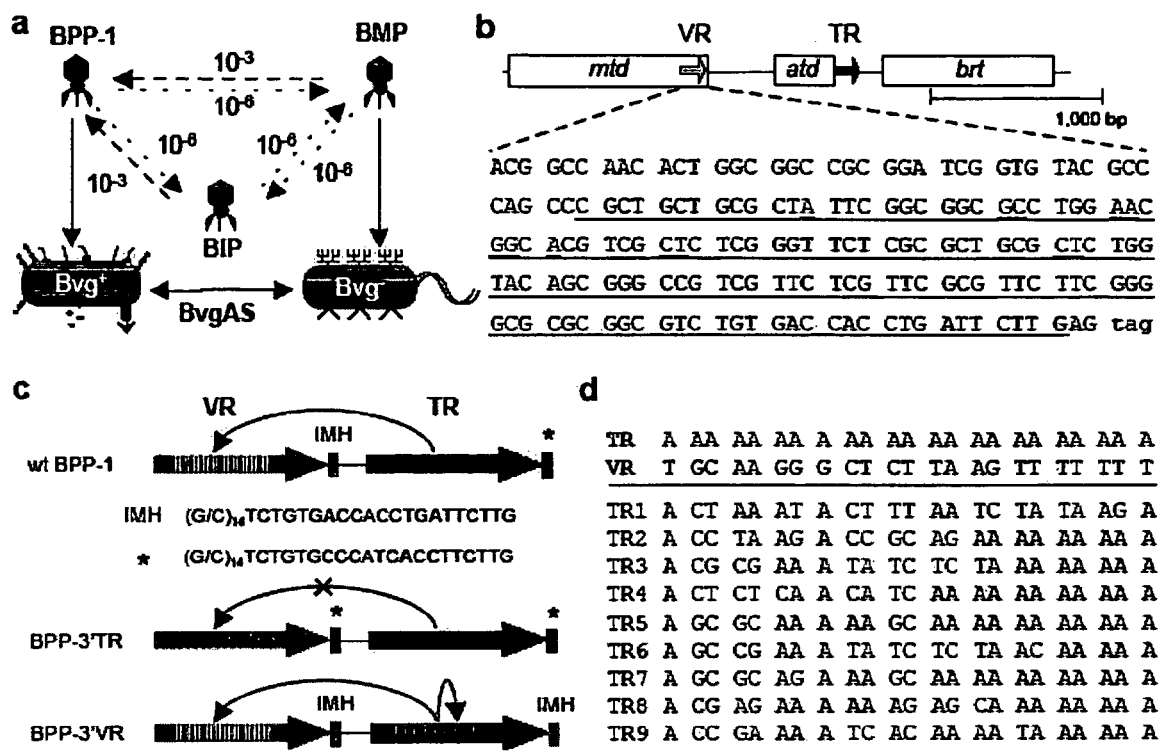
FIGS. 1a to 1d show tropism switching by *Bordetella* bacteriophage.
Figure 2A:
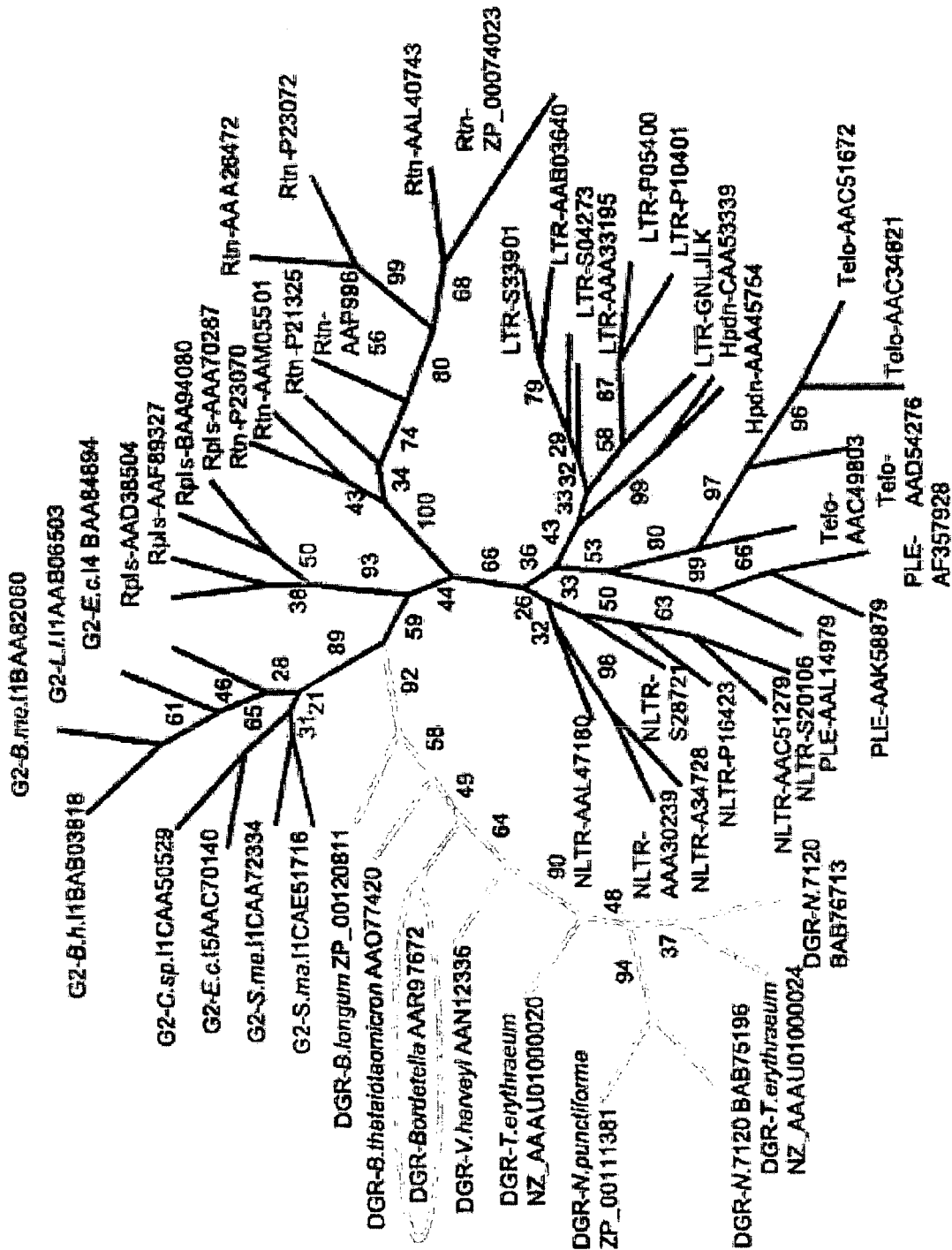
FIGS. 2a and 2b show diversity-generating retroelements (DGRs) in bacterial and bacteriophage genomes.
Figure 2B:
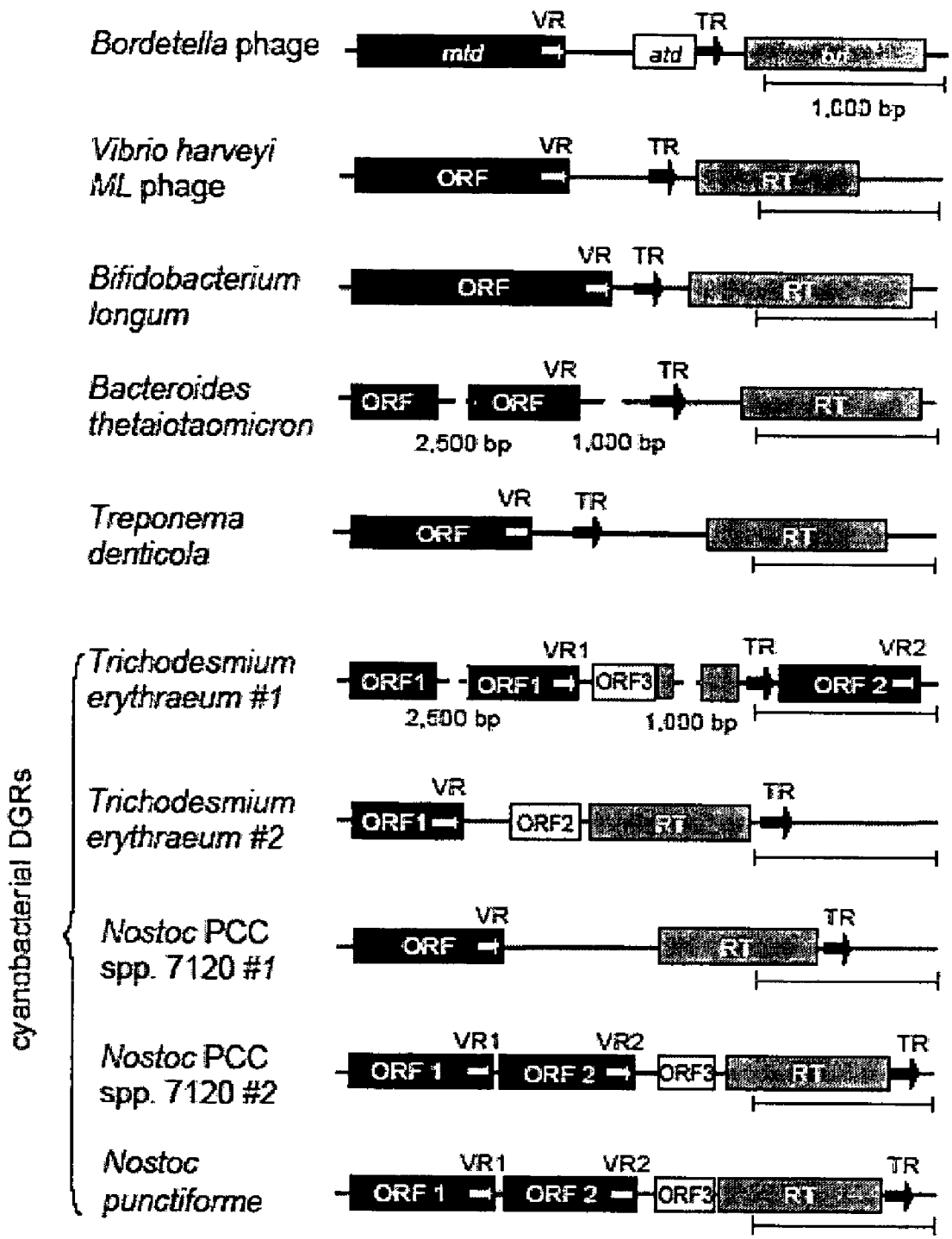
Figure 3:
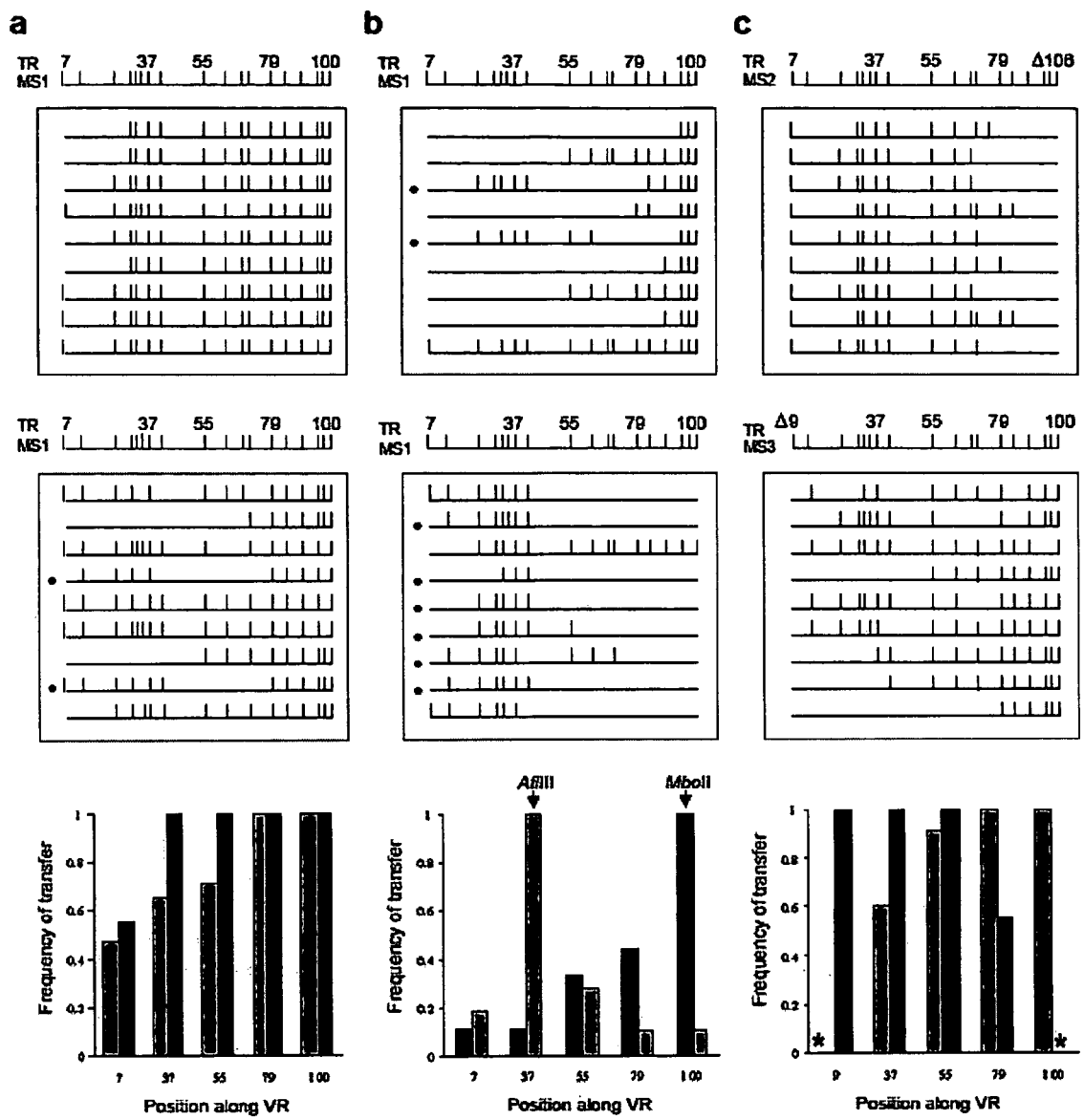
FIGS. 3a-3c show the results of multiple substitution experiments.
Figure 8:
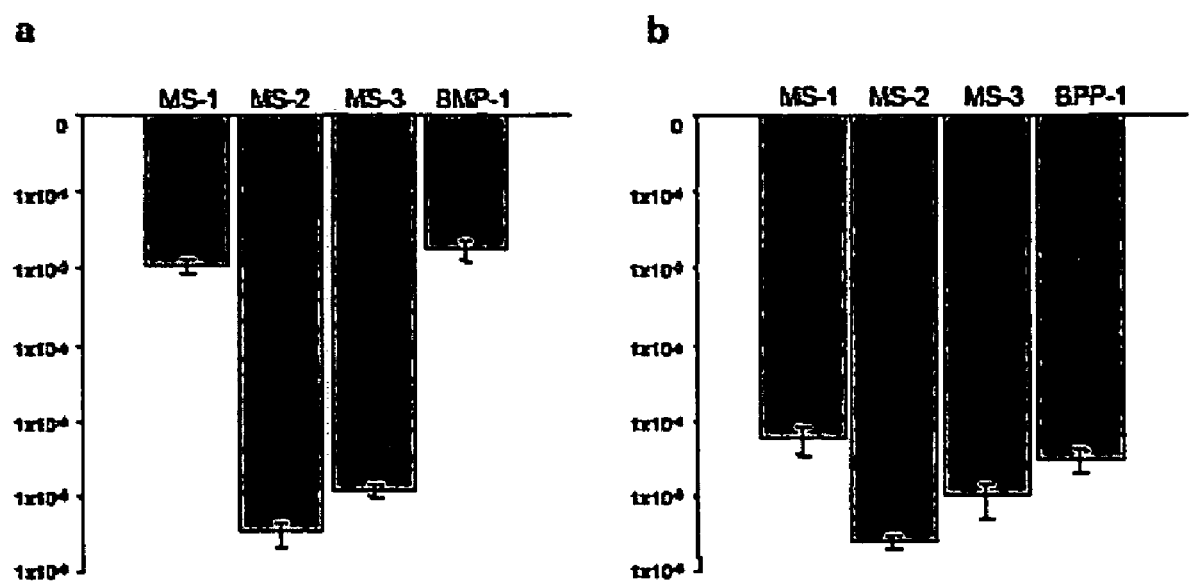
Figure 10:
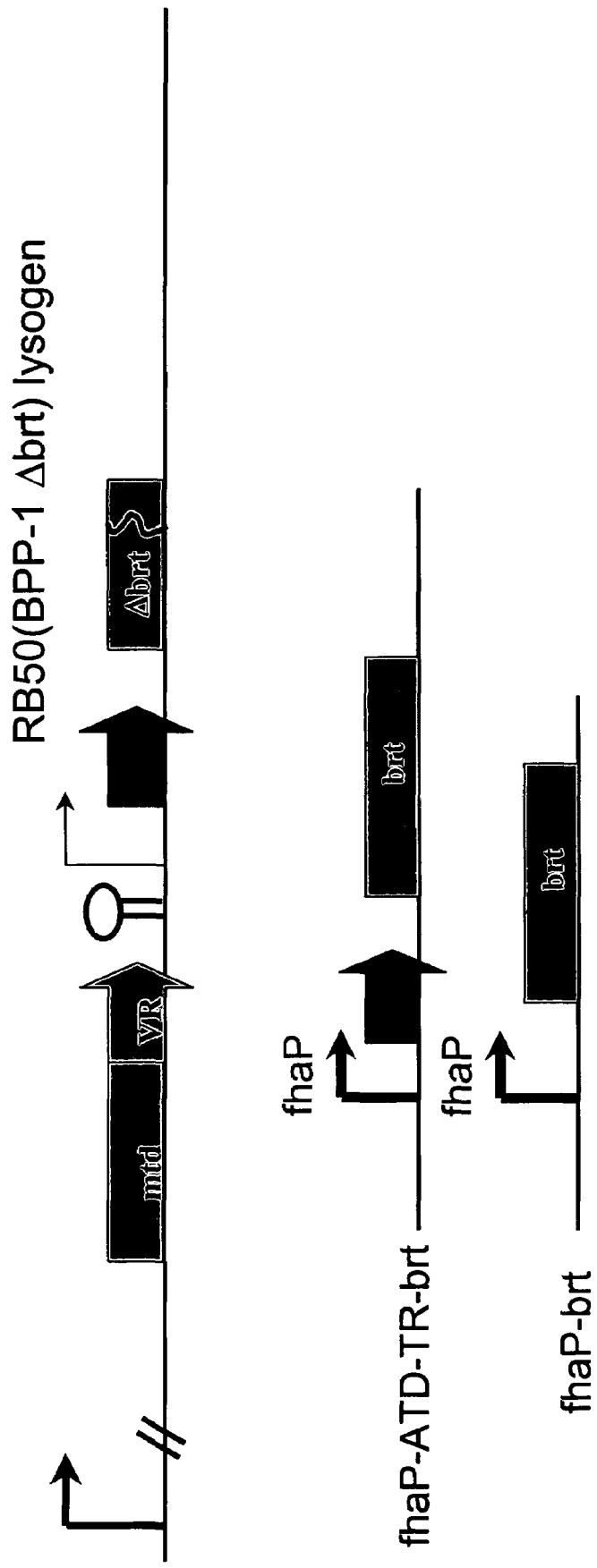
Figure 11:
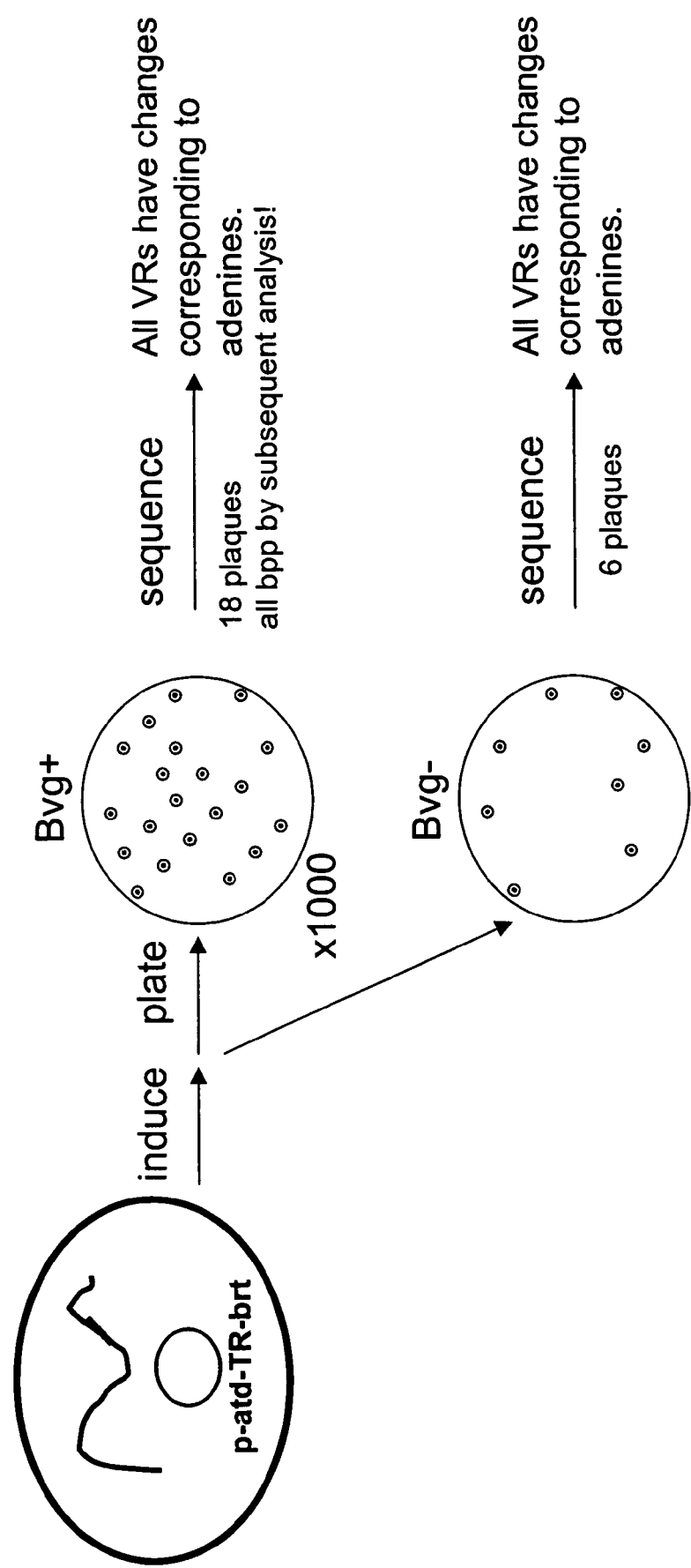
Figure 12:
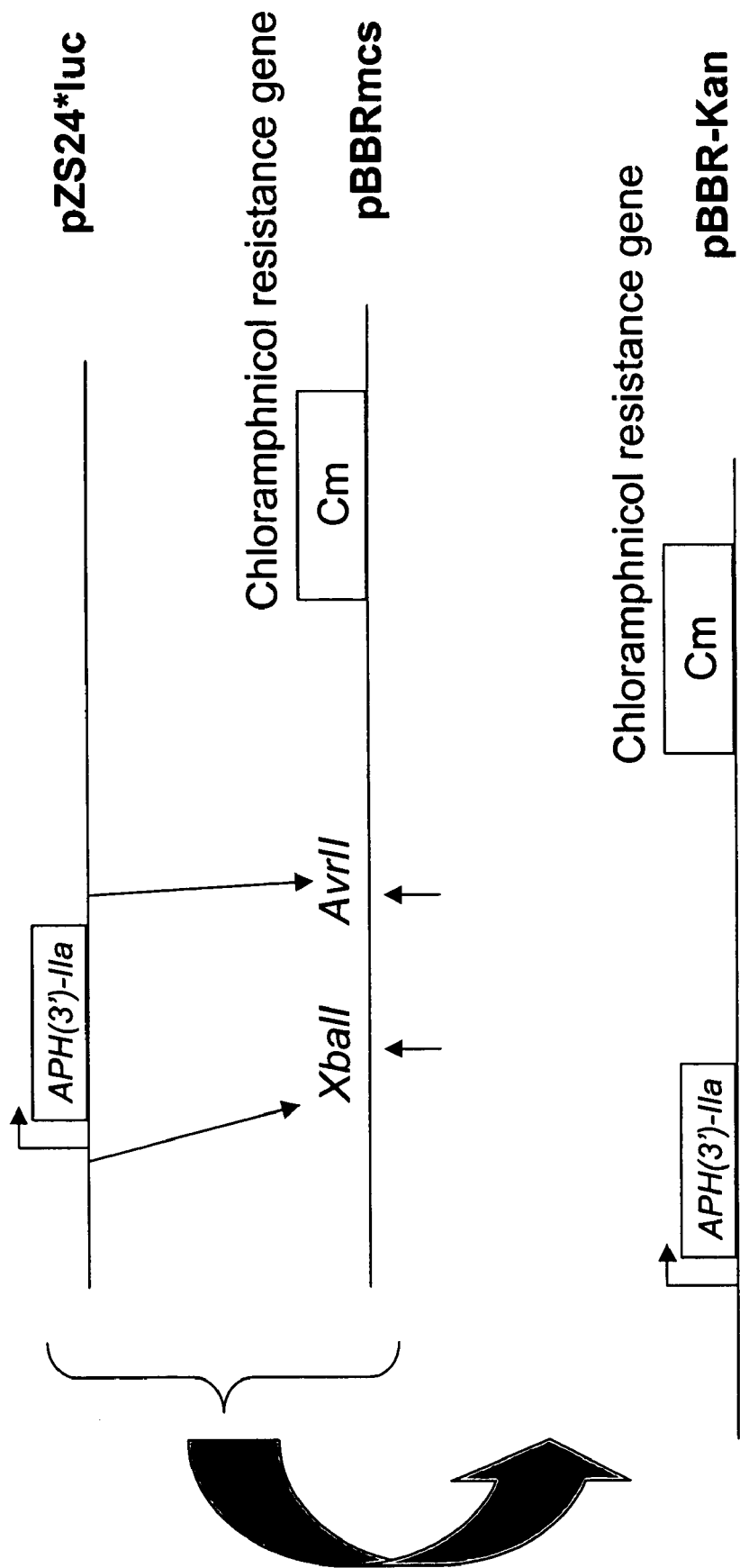

The system surprisingly accommodated these rather extreme selections. Both mutant phages were able to switch tropism while avoiding the transmission of frameshift mutations, generating transmission histograms that are essentially mirror images (FIGS. 3c and FIG. 8).

Example 3

Gene Conversion

Figure 4:
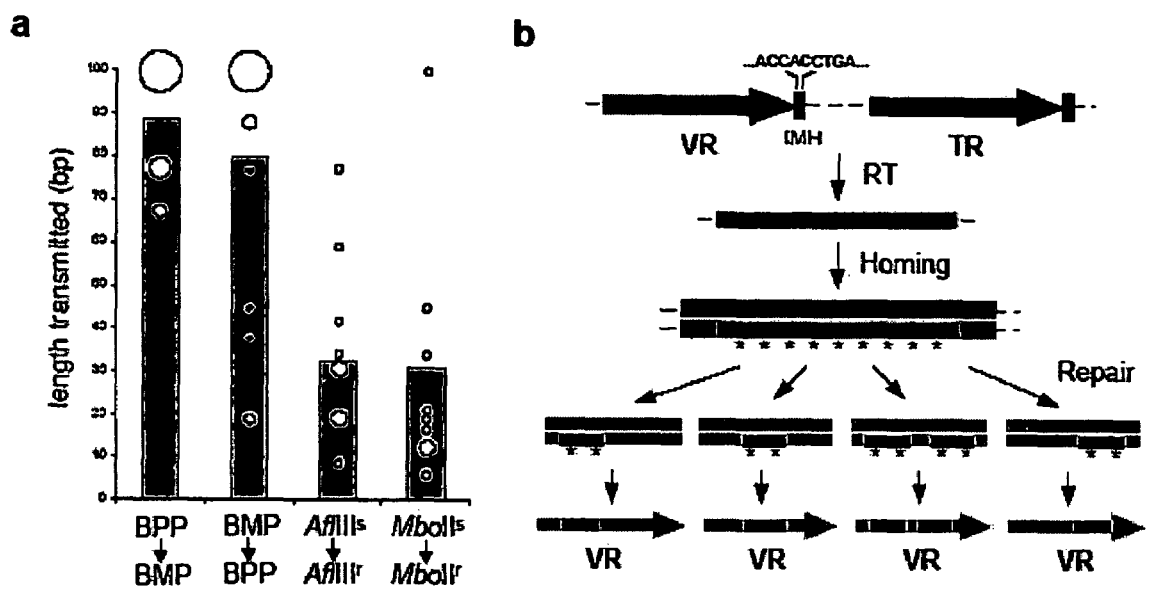
FIGS. 4a and 4b show mosaic VR sequences result from mutagenic homing.

Selection at a single position, as imposed by in vitro restriction enzyme-based assays, tends to isolate shorter variable sequences centered around the point of selection. More complex selections for novel receptor specificity select for larger segments of transferred, mutagenized sequence (FIG. 4a).

These conditions could be satisfied by a mechanism in which site-specific homing, initiated at IMH, is followed by random gene conversion due to recombination or repair. According to this model, a heteroduplex is formed at VR during the variability generating process (FIG. 4*b*). See Morrish, et al. and Wank, et al. The heteroduplex would be characterized by a high density of mismatched basepairs resulting from the hybridization of VR with a TR-derived cDNA. Mismatch repair, or an analogous process, would give rise to chimeric VRs containing "patches" of sequence variation.

A consequence of the diversity-generating mechanism is that variability is introduced into the mtd locus in a highly targeted manner. Diversification exclusively occurs within the boundaries of the variable repeat, it only occurs at positions corresponding to adenine residues in TR, and it can be limited to the subset of bases that are subject to selection. This "focusing" of variability has the potential to be highly adaptive as it provides a means to efficiently respond to selective pressures while minimizing the accumulation of unnecessary or deleterious substitutions. The repair step may be essential given the high rate of adenine-mutagenesis, and it allows optimization of receptor specificity through iterative rounds of selection (Wrighton, N. C. et al. Small peptides as potent mimetics of the protein hormone erythropoietin. *Science* 273, 458-64 (1996) and Fairbrother, W. J. et al. Novel peptides selected to bind vascular endothelial growth factor target the receptor-binding site. *Biochemistry* 37, 17754-17764 (1998)).

Example 4

Related Gene Diversification Systems in Other Organisms

The ability to diversify protein domains involved in ligand-receptor interactions has extremely broad utility. The invention thus provides elements homologous to the *Bordetella* phage retroelement as discovered from other sources in nature. To identify related sequences, open reading frames (ORFs) of bacterial origin containing conserved RT domains were compiled. A subset clustered phylogenetically with Brt (FIG. 2*a*). Adjacent sequences were examined and in all cases candidate TR and VR repeats were identified, with VRs located at the 3' end of an ORF.

Further annotation revealed an array of cassettes which we now designate as putative diversity generating retroelements (DGRs). Although RT domains are highly related, and DGRs share an overall conservation of structural features (FIG. 4*b*), there is little if any sequence similarity between other components of these related cassettes.

In every case VR analogs differ from their cognate TRs almost exclusively at positions corresponding to adenines (FIG. 9). This observation supports the use of these cassettes based on their function to generate diversity in a similar manner.

Comparison of the 3' ends of cognate VRs and TRs also suggests the presence of analogous sequences to the *Bordetella* phage IMH site (FIG. 9). As shown in FIG. 2*b*, DGRs are found in the chromosomes of a wide array of bacterial species and they display variations on a common theme. For example, *Nostoc* and *Trichodesmium* species contain cassettes in which a single TR apparently supplies two different VRs with sequence variability. In such cases, the VRs are part of paralogous ORFs with over 90% sequence identity and are identical except for bases corresponding to adenines in TR.

In addition, several cyanobacterial species contain multiple DGRs which are not homologous and have, therefore, been independently acquired. Although the *Bordetella* and *V. harveyi* cassettes are present on prophage genomes, there is no evidence of phage association for the remaining sequences. On the basis of the data in FIG. 2, it is proposed that DGRs have evolved to perform myriad functions in diverse organisms.

Retroelements such as group II introns (Bonen, L. & Vogel, J. The ins and outs of group II introns. *Trends Genet* 17, 322-331 (2001)), retrotransposons (Bushman, F. D. Targeting survival: integration site selection by retroviruses and LTR retrotransposons *Cell* 115, 135-138 (2003)), retroviruses (Gifford, R. & Tristem, M. The evolution, distribution and diversity of endogenous retroviruses. *Virus Genes* 26, 291-315 (2003)), and human LINEs (Kazazian, H. H. Jr. & Goodier, J. L. LINE drive: retrotransposition and genome instability *Cell* 110, 277-280 (2002)) share related characteristics.

Example 5

Elements of the DGR which Act in Cis and Trans

*Bordetella* strain 61-11 (RB50 BPP-1 Δbrt, see FIG. 10) was used to characterize cis and trans acting elements of the DGR. The strain carries a deletion in the prophage RT gene (brt) which renders the phage unable to switch its tropism.

DNA fragments containing various components of the DGR were amplified by PCR from the intact RB50 BPP-1 lysogen, digested with restriction enzymes and cloned into the vector pBBRmcsF carrying an fha promoter. Two of the plasmids, pfhaP-atd-TR-brt and pfhaP-TR-brt, are shown in Table 1 and schematically in FIG. 10. In pfhaP-atd-TR-brt, there is no terminator between the fhaP and atd-TR-brt sequences. In pfhaP-TR-brt, there is no atd between the fha promoter and the TR sequence.

The resulting constructs are listed in Table 2.

TABLE 2

| plasmid: | | Primers used for constructions: | Causes tropism switching in strain 61-11: |
|---|---|---|---|
| pfhaP-atd-TR-brt | the atd-TR-brt region in DGR is cloned in vector pBBRmcsF | atd-TRHindIII for BrtBamHrev | yes |
| pfhaP-TR-brt | the TR-brt region in DGR is cloned in vector pBBRmcsF | TRHindIII for BrtBamHrev | yes |

TABLE 2-continued

| plasmid: | | Primers used for constructions: | Causes tropism switching in strain 61-11: |
|---|---|---|---|
| pfhaP-brt | only the brt region in DGR is cloned in vector pBBRmcsF | BrtXbal for BrtSacl rev | no |
| pfhaP-atd-TR | the atd-TR region in DGR is cloned in vector pBBRmcsF | | no |

After transformation of plasmids into strain 61-11, tropism switching was assayed by inducing lysogenic cells with mitomycin C and plating the phage lysate directly onto RB53 (a Bvg+ strain) or RB54 (a Bvg− strain) to observe plaque formation (see FIG. 11 for a representation of the use with pfhaP-atd-TR-brt).

Induced lysate from cells harboring the pfhaP-atd-TR-brt was plated directly on RB53(Bvg+) or RB54(Bvg−). Eighteen (18) plaques from RB53 plates were isolated and, after PCR amplification, their VR regions were sequenced and found to have changes at positions corresponding to adenines in the TR. From 100 μl of lysate, an average of 15 plaques were seen by plating directly on RB54 (efficiency compared to plating on RB53 is about $10^{-3}$).

In parallel, induced lysate from cells harboring the pfhaP-TR-brt was also directly plated on RB53(Bvg+) or RB54 (Bvg−). Phages from 10 plaques from RB53 plates were isolated, their VR regions amplified by PCR and sequenced. All had changes in VR regions corresponding to adenines in the TR. From 100 μl of lysate, an average of 15 plaques were seen by plating directly on RB54 (efficiency compared to plating on RB53 is about $10^{-3}$)

Because the VR regions of all of the phages, even those that did not switch tropism, contained nucleotide changes corresponding to adenine residues in the TR, the frequency of mutagenesis was effectively 100% with the use of a strong heterologous promoter.

Similar experiments with pfhaP-brt and pfhaP-atd-TR showed no tropism switching.

The results show that the minimal unit required for complementation of the brt deletion, restoring the ability to switch tropism, is the TR-brt region, in which:

(i) The TR acts in cis with brt (ii) The TR acts in trans to the VR

The results further suggest that the trans acting construct was able to direct the mutagenesis of a proviral copy of the phage VR sequence.

Example 6

Mutagenesis in Trans of an Uninduced Prophage

The ability of trans expression of TR-brt to alter the VR sequence of a (chromosomal) prophage was determined in the absence of phage induction. In the uninduced lysogen 61-11 harboring the plasmid pfhaP-atd-TR-brt, PCR amplification was performed on an overnight culture and DNA products were cloned into a sequencing vector.

In one experiment, one colony was picked and grown by overnight culture in LB medium at 37° C. The VR region of 5 μl overnight culture was PCR amplified and cloned into a sequencing vector (pBluesriptII). 20 plasmids were sequenced, with 2 (thus 10%) having changes in the VR corresponding to adenines in the TR. In another experiment, 5 colonies were picked and individually grown via overnight culture in LB medium at 37° C. The VR region of 5 μl of each overnight culture was PCR amplified and cloned into a sequencing vector (pBluesriptII). Three (3) plasmids from each plating were sequenced, with 5 of 15 (thus 30%) having changes in the VR corresponding to adenines in the TR.

Thus, fha promoter-directed transcription of the TR-brt region results in elevated levels of VR mutagenesis, demonstrating that:

(i) TR-brt transcription can be placed under the control of a heterologous promoter, replacing the need for the atd element (see below)

(ii) Control of TR-brt transcription affects the levels of VR mutagenesis (iii) The TR-brt region can act in trans on a cognate VR in the bacterial chromosome

Example 7

Introduction of Added Sites of Mutagenesis

Using site-directed mutagenesis, 3 adenines were substituted for nucleotides 59-61 of the TR region. The corresponding VR nucleotides encoded non-variable Mtd residue A356. Using homologous recombination, the TR with 3 adenines substituted was introduced into strain 6405 (RB54 BMP-1 lysogen). Successful modification of the 6405 TR was confirmed by sequencing and restriction digestion, generating strain 6405AAA (see below).

TR—strain 6405

(SEQ ID NO:34)

```
cgctgctgcgctattcggcggcaactggaacaacacgtcgaactcgggtt
ctcgcgctGCGaactggaacaacgggccgtcgaactcgaacgcgaacatc
ggggcgcgcggcgtctgtgcccatcaccttcttg
```

TR—strain 6405AAA (SEQ ID NO:35)

```
cgctgctgcgctattcggcggcaactggaacaacacgtcgaactcgggtt
ctcgcgctAAAaactggaacaacgggccgtcgaactcgaacgcgaacatc
ggggcgcgcggcgtctgtgcccatcaccttcttg
```

Strain 6405AAA was induced, VR regions of the resulting phage mixture were PCR amplified and digested with a restriction enzyme (MboII) that cuts the parental VR sequence 3' to the AAA substitution. The in vitro selection was for diversification of the parental MboII recognition sequence without assessing its effect on the encoded polypeptide. Re-amplification of VR sequences undigested by MboII followed by cloning and sequencing demonstrated that the newly introduced TR adenine residues were transmitted to VR and diversified.

Example 8

The atd is not Required for Homing Mutagenesis

Placement of a stop codon into atd does not eliminate mutagenesis. This indicates that the atd does not encode a protein required for mutagenesis.

Using site-directed mutagenesis, a stop codon was substituted for the 9th amino acid of the postulated accessory tropism determinant (atd) ORF. Using homologous recombination, the atd with a stop codon was introduced into lysogen strain 6405. Successful modification of the 6405 was confirmed by sequencing.

After induction and an additional round of propagation, phages able to plaque on either BVG+ and BVG− *Bordetella bronchiseptica* were isolated. Therefore, the phage maintained the ability to switch tropism. In -continued

```
TR'        cttgacaagaacttctgaTCGAACTCGAACGCGAACATCGGGGCGCGCGGCGTCTGTGCC
243amVR    cttgacgagttcttctgaTCGTTCTCGTTCGCGTTCTTCGGGGCGCGCGGCGTCTGTGAC TR'        CATCACCTTCTTG (SEQ ID NO:39)
243amVR    CACCTGATTCTTG (SEQ ID NO:40)
```

Figure 13:
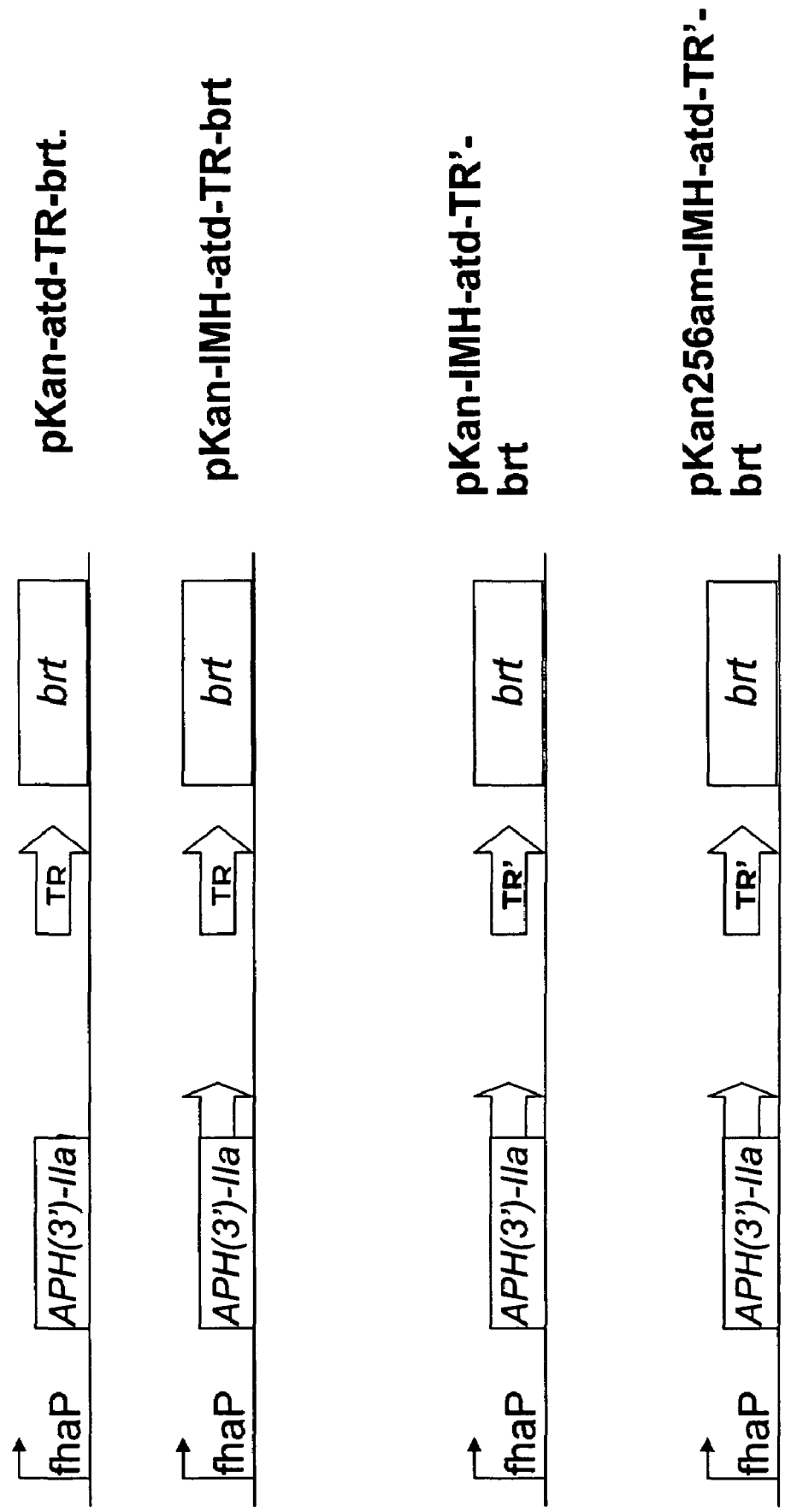

The TR' region for the kanamycin resistance gene in plasmid pKan-IMH-atd-TR-brt was made by modified site-directed mutagenesis. The final plasmid is pKan-IMH-atd-TR'-brt (FIG. 13) or pKan-TR'. An amber stop codon was introduced into the kanamycin resistance gene at position 243 by site-directed mutagenesis to produce pKan243am-IMH-atd-TR'-brt (also referred to as pKan243-TR').

The plasmid was transformed into lysogen 61-11. The lysogen with plasmid pKan-TR' grew normally in the presence of kanamycin.

Selection of kanamycin resistance with pKan243-TR' was as follows. A culture of lysogen 61-11 carrying plasmid pKan243-TR' was grown overnight followed by serial dilution. The dilutions were plated on LB plates with 40 µg/ml kanamycin. The 61-11 hosts harboring kanamycin resistant plasmids that have "repaired" the amber stop codon by adenine-specific mutagenesis, would be expected to form colonies in the presence of kanamycin. Two robust colonies, 243resis1VR and 243resis2VR, from the plate of hosts harboring pKan243-TR' were isolated, and, their VR regions were amplified and sequenced.

The results are as shown in the box immediately above, where 243resis1VR contained a taa to tac(Tyr) change; tac is the same codon sequence as that in TR'. This indicates that the TR' sequence was used to substitute for the VR sequence. Stated differently, the change was the result of sequence substitution from the TR' to the VR.

In 243resis2VR, taa was changed to ttc(Phe), the result of 2 mutations in the same codon. One of the 2 mutagenic events was an A to T change resulting from diversification of the corresponding A in TR' while the A to C change was a substitution (or homing) from the TR' template as seen for 243resis1VR. Phe and Tyr have very similar amino acid structures and are both hydrophilic, and the results show that a Tyr or Phe at position 243, which is Leu (also hydrophilic) in the native sequence, was able to restore kanamycin resistance. This suggests that position 243 tolerates a Leu to Tyr or Phe substitution for maintenance or restoration of phosphotransferase function.

As shown by Nurizzo et al. (J. Mol. Biol., 327:491-506, 2003), the C-terminal domain of the kanamycin resistant protein is involved in binding the kanamycin molecule. According to their published crystal structure, the L243 to amber mutation truncates the protein prior to alpha helices 7 and 8. This leads to loss of C-terminal residues 260-264, which form part of the kanamycin-binding pocket. Thus the sequence changes from a stop codon to those in 243resis1VR and 243resis2VR reflect restoration of the kanamycin binding domain of the phosphotransferase.

The above results also indicate that the IMH does not need to be translated for mutagenesis to occur because the IMH follows a tga stop codon in the above kanamycin phosphotransferase constructs. The above described results may also be performed with a trans construct which provides the TR and RT coding sequences under the control of a separate promoter on a second molecule.

Example 10

Identification of a DGR from T. denticola

Treponema denticola is a motile, anaerobic spirochete that colonizes the human oral cavity and has been associated with gum disease. There is a 134 base pair identified variable region (VR) located at the 3' end of open reading frame TDE2269. A corresponding template region (TR) is located 199 base pairs downstream of the VR and 573 base pairs upstream of a reverse transcriptase coding sequence that bears homology (6e-39) to the Bordetella phage reverse transcriptase (brt). The VR and TR differ at 26 positions, with 23 of those differences occurring in the VR at positions that correspond to adenines within the TR. Two of the three positions that do not correspond to adenines may be a part of the IMH signal since they are the most 3' positions of variability (see below). Also, TDE2269 has a lipoprotein signal sequence (underlined below) indicating that this protein may be exported to the outer membrane. The VR is shown in bolded text below.

TDE2269-329 Amino Acids (SEQ ID NO:41)
MKNTNSKLKTKVLNRAISITALLLAAGVLLTGCPTGQGKSGGGESSEVTP

NTPVDKTYTVGSVEFTMKGIAAVNAQLGHNDYSINQPHTVSLSAYLIGET

EVTQELWQAVMGNNPSHFNGSPAVGETQGKRPVENVNWYQAIAFCNKLSI

KLNLEPCYTVNVGGNPVDFAALSFDQIPDSNNADWDKAELDINKKGFRLP

TEAEWEWAAKGGTDDKWSGTNTEAELKNYAWYGSNSGSKTHEVKKKKPNW

YGLYDIAGNVAEWCWDWRADIHTGDSFPQDYPGPASGSGRVLRGGSWAGS

ADYCAVGERVNISPGVRCSDLGFRLACRP

To confirm variation in the VR corresponding to adenines in the TR, the restriction enzyme HincII was used in a variability assay to identify a T. denticola VR that differs from the sequenced VR at 25 nucleotide positions. Twenty-one of the 25 differences occur at positions that correspond to adenines within the TR, and one of the remaining four differences appears to be a direct nucleotide transfer (or homing) from the TR as shown below.

The HincII recognition site is GTYRAC (SEQ ID NO:42) where Y is C or T; and R is A or G. TR stands for Template Region; VR stands for Variable Region; and IV stands for Identified Variant of Variable Region. A portion of presumptive IMH-like and IMH sequences of TR and VR, respectively, are shown in bold type.

```
TR: CCGCGTCAGGCTCTAACCGTGTTAAACGCGGCGGCAGCTGGAACAACAACGCGAACAA
VR: CCGCGTCAGGCTCTGGCCGTGTTTTACGCGGCGGCAGCTGGGCCGGCAGCGCGGACTA
IV: ----------------------------------------A-AA-TA------GGG

TR: CTGCACTGTAGGCAAACGGAATAACAACAGTCCTGACAACAGGAACAACAATCTTGGC
VR: CTGCGCTGTAGGCGAACGGGTCAACATCAGTCCTGGCGTCAGGTGCAGCGATCTTGGC
IV: ----A----G---ACC----GT---GG--AC------AA----G---A-CT-------

TR: TTCCGCTTGGCTTGTCGGCC  (SEQ ID NO:43)
VR: TTCCGCCTGGCTTGCCGGCC  (SEQ ID NO:44)
IV: --------------------  (SEQ ID NO:45)
```

All references cited herein are hereby incorporated by reference in their entireties, whether previously specifically incorporated or not. As used herein, the terms "a", "an", and "any" are each intended to include both the singular and plural forms.

Having now fully described this invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A single recombinant nucleic acid molecule or pair of recombinant nucleic acid molecules comprising a variable region (VR) operably linked to a donor template region (TR)

wherein said TR comprises an imperfect repeat of the sequence in said VR due to the substitution of non-adenine nucleotides in VR at positions corresponding to one or more adenine nucleotides in TR and said TR is operably linked to a reverse transcriptase (RT) coding sequence which said RT directs at sites of adenine in said TR site-specific mutagenesis of said VR, and wherein the TR and RT coding sequence are heterologous to each other.

2. The molecule of claim 1, wherein said VR is all or part of a sequence encoding a specific binding partner of a target molecule.

3. The molecule of claim 2, further comprising all of the sequence encoding said binding partner, wherein said VR is optionally the 3' portion of said sequence encoding said binding partner.

4. The molecule of claim 2, wherein said binding partner binds a cell surface molecule, a hormone, a growth or differentiation factor, a receptor, a ligand of a receptor, a bacterial cell wall molecule, a viral particle, an immunity or immune tolerance factor, or an MHC molecule.

5. The molecule of claim 2, wherein said binding partner is a bacteriocin.

6. The molecule or pair of molecules of claim 1, wherein said TR and RT coding sequences are transcribed under the control of a heterologous promoter, such as the fha promoter.

7. A cell containing the molecule or pair of molecules of claim 1.

8. A plurality or library of nucleic acid molecules according to claim 1.

9. The plurality or library of claim 8, wherein the VR has undergone diversification directed by the TR.

* * * * *

UNITED STATES PATENT AND TRADEMARK OFFICE
CERTIFICATE OF CORRECTION

PATENT NO. : 7,585,957 B2 Page 1 of 1
APPLICATION NO. : 11/197219
DATED : September 8, 2009
INVENTOR(S) : Miller et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 577 days.

Signed and Sealed this

Fourteenth Day of September, 2010

David J. Kappos
*Director of the United States Patent and Trademark Office*

SEQUENCE LISTING

```
<160> NUMBER OF SEQ ID NOS: 103

<210> SEQ ID NO 1
<211> LENGTH: 43
<212> TYPE: DNA
<213> ORGANISM: Bacteriophage BPP-1

<400> SEQUENCE: 1
gcgaacatcg gggcgcgcgg cgtctgtgcc catcaccttc ttg                43

<210> SEQ ID NO 2
<211> LENGTH: 48
<212> TYPE: DNA
<213> ORGANISM: Bacteriophage BPP-1

<400> SEQUENCE: 2
gcgttcttcg gggcgcgcgg cgtctgtgac cacctgattc ttgagtag          48

<210> SEQ ID NO 3
<211> LENGTH: 24
<212> TYPE: DNA
<213> ORGANISM: Bifidobacterium Longum

<400> SEQUENCE: 3
tggaacatcg ggggccgcat atcc                                    24

<210> SEQ ID NO 4
<211> LENGTH: 48
<212> TYPE: DNA
<213> ORGANISM: Bifidobacterium Longum

<400> SEQUENCE: 4
tggcacctcg ggggccgcct ttctgcgctc ggtcgcacga aggcgtag           48

<210> SEQ ID NO 5
<211> LENGTH: 45
<212> TYPE: DNA
<213> ORGANISM: Bacteriodes thetaiotaomicron
```

-continued

```
<400> SEQUENCE: 5
acaacaatcg gcgtacggg tttggggtgc gttcttccca agaat              45

<210> SEQ ID NO 6
<211> LENGTH: 47
<212> TYPE: DNA
<213> ORGANISM: Bacteriodes thetaiotaomicron

<400> SEQUENCE: 6
actactctcg ggcgtgcggg tttgggttgc gttcttccca agaatag           47

<210> SEQ ID NO 7
<211> LENGTH: 32
<212> TYPE: DNA
<213> ORGANISM: Vibrio harveyi phage

<400> SEQUENCE: 7
aatagcatcg gttttcgccc cgctcttgat gt                           32

<210> SEQ ID NO 8
<211> LENGTH: 36
<212> TYPE: DNA
<213> ORGANISM: Vibrio harveyi phage

<400> SEQUENCE: 8
agtagcatcg gttttcgccc cgctttcttt gtgtaa                       36

<210> SEQ ID NO 9
<211> LENGTH: 36
<212> TYPE: DNA
<213> ORGANISM: Treponema denticola

<400> SEQUENCE: 9
gacaacaatc ttggcttccg cttggcttgt cggccc                       36

<210> SEQ ID NO 10
<211> LENGTH: 39
<212> TYPE: DNA
<213> ORGANISM: Treponema denticola

<400> SEQUENCE: 10
tgcagcgatc ttggcttccg cctggcttgc cggccttaa                    39

<210> SEQ ID NO 11
<211> LENGTH: 53
<212> TYPE: DNA
<213> ORGANISM: Trichodesmium erythraeum #2

<400> SEQUENCE: 11
cgagtcatct cgtcttcccc ggtggtttct ggctttcatt cctagtattc ttc    53

<210> SEQ ID NO 12
<211> LENGTH: 53
<212> TYPE: DNA
<213> ORGANISM: Trichodesmium erythraeum #2

<400> SEQUENCE: 12
cgagtcatct cctcttcccc ggtggtttct ggctttcatt cctagtattc ttc    53

<210> SEQ ID NO 13
<211> LENGTH: 46
<212> TYPE: DNA
<213> ORGANISM: Trichodesmium erythraeum #1
```

<400> SEQUENCE: 13
caacaatatt ggttttcgtc ttgtgagttt cccccccagc actctt    46

<210> SEQ ID NO 14
<211> LENGTH: 52
<212> TYPE: DNA
<213> ORGANISM: Trichodesmium erythraeum #1

<400> SEQUENCE: 14
catcaatttt ggttttcgtc ttgtgagttt cccccccagg actcttgaat ag    52

<210> SEQ ID NO 15
<211> LENGTH: 48
<212> TYPE: DNA
<213> ORGANISM: Trichodesmium erythraeum #1

<400> SEQUENCE: 15
cgactttgtt ggttttcgtc ttgtgagttt cccccccagg actcctga    48

<210> SEQ ID NO 16
<211> LENGTH: 48
<212> TYPE: DNA
<213> ORGANISM: Nostoc. spp. 7120 #1

<400> SEQUENCE: 16
aacaatattg gttttcgtgt tgtctgcgcg ttcgggagta ctcttcac    48

<210> SEQ ID NO 17
<211> LENGTH: 51
<212> TYPE: DNA
<213> ORGANISM: Nostoc. spp. 7120 #1

<400> SEQUENCE: 17
tacagttttg gttttcgtgt tgtctgcgcg ttcgggagga ttcttcagta g    51

<210> SEQ ID NO 18
<211> LENGTH: 51
<212> TYPE: DNA
<213> ORGANISM: Nostoc. spp. 7120 #1

<400> SEQUENCE: 18
tacgctgttg gttttcgtgt tgtctgcgcg ttcgggagga cttttcagta g    51

<210> SEQ ID NO 19
<211> LENGTH: 47
<212> TYPE: DNA
<213> ORGANISM: Nostoc punctiforme

<400> SEQUENCE: 19
aacaatattg gttttcgtgt tgtctgcgcg ttcgggatgt ctcttca    47

<210> SEQ ID NO 20
<211> LENGTH: 51
<212> TYPE: DNA
<213> ORGANISM: Nostoc punctiforme

<400> SEQUENCE: 20
agcaatgttg gttttcgtgt tgtctgcgcg ttcgggagga ttcttcagta g    51

<210> SEQ ID NO 21
<211> LENGTH: 51
<212> TYPE: DNA

<213> ORGANISM: Nostoc punctiforme

<400> SEQUENCE: 21
agcactcttg gttttcgtgt tgtctgcgcg ttcgggagga ttcttcagta g    51

<210> SEQ ID NO 22
<211> LENGTH: 36
<212> TYPE: DNA
<213> ORGANISM: Nostoc. spp. 7120 #2

<400> SEQUENCE: 22
caacgtaggt tttcggggttg tggttgtgcg gggcag    36

<210> SEQ ID NO 23
<211> LENGTH: 46
<212> TYPE: DNA
<213> ORGANISM: Nostoc. spp. 7120 #2

<400> SEQUENCE: 23
gcgcgtgggt tgtcggggttg tggttgtgcg gggcaggctt tcttag    46

<210> SEQ ID NO 24
<211> LENGTH: 57
<212> TYPE: DNA
<213> ORGANISM: Chlorobium phaeobacteroides

<400> SEQUENCE: 24
aacaatatcg gttttcgtgt tgttcgtccc aatcatgccc gttttatggt gcggtaa    57

<210> SEQ ID NO 25
<211> LENGTH: 54
<212> TYPE: DNA
<213> ORGANISM: Chlorobium phaeobacteroides

<400> SEQUENCE: 25
ggcgttatcg gttttcgtgt tgttcgtccc agtcatcttt tgtgattatc tgat    54

<210> SEQ ID NO 26
<211> LENGTH: 56
<212> TYPE: DNA
<213> ORGANISM: Chlorobium phaeobacteroides

<400> SEQUENCE: 26
tacggtttcg gttttcgtgt tgttcgtccc agtcatcttt tgtgattatc tgatac    56

<210> SEQ ID NO 27
<211> LENGTH: 59
<212> TYPE: DNA
<213> ORGANISM: Pelodictyon phaeoclathratiforme

<400> SEQUENCE: 27
aacaatattg gctttcgggt tgtccgttcc aatcatgccc tttcgatgc gtgttaaag    59

<210> SEQ ID NO 28
<211> LENGTH: 59
<212> TYPE: DNA
<213> ORGANISM: Pelodictyon phaeoclathratiforme

<400> SEQUENCE: 28
ggcaatgttg gctttcgggt tgtccgttcc agtccctctt cctgatcttc tgtctttct    59

<210> SEQ ID NO 29
<211> LENGTH: 59

```
<212> TYPE: DNA
<213> ORGANISM: Prosthecochloris aestuarii

<400> SEQUENCE: 29
acaacaattt gggcttccgg gttgtgagta caaagtatcg ccagatgggg attgtttac      59

<210> SEQ ID NO 30
<211> LENGTH: 53
<212> TYPE: DNA
<213> ORGANISM: Prosthecochloris aestuarii

<400> SEQUENCE: 30
acgacgtttt gggcttccgc cttgtgaggc agccttagta tcccttgggg ttt           53

<210> SEQ ID NO 31
<211> LENGTH: 59
<212> TYPE: DNA
<213> ORGANISM: Prosthecochloris aestuarii

<400> SEQUENCE: 31
acgacgattt gggcttccgc cttgtgaggc agccttagta tctcttgggg ttttacca      59

<210> SEQ ID NO 32
<211> LENGTH: 7
<212> TYPE: PRT
<213> ORGANISM: Artificial Sequence
<220> FEATURE:
<223> OTHER INFORMATION: Conserved nucleotide binding site motif
<220> FEATURE:
<221> NAME/KEY: MISC_FEATURE
<222> LOCATION: (3)..(5)
<223> OTHER INFORMATION: Any naturally occurring amino acid

<400> SEQUENCE: 32

Ile Gly Xaa Xaa Xaa Ser Gln
1               5

<210> SEQ ID NO 33
<211> LENGTH: 7
<212> TYPE: PRT
<213> ORGANISM: Artificial Sequence
<220> FEATURE:
<223> OTHER INFORMATION: Conserved nucleotide binding site motif
<220> FEATURE:
<221> NAME/KEY: MISC_FEATURE
<222> LOCATION: (3)..(5)
<223> OTHER INFORMATION: Any naturally occurring amino acid

<400> SEQUENCE: 33

Leu Gly Xaa Xaa Xaa Ser Gln
1               5

<210> SEQ ID NO 34
<211> LENGTH: 134
<212> TYPE: DNA
<213> ORGANISM: RB54 BMP-1 lysogen

<400> SEQUENCE: 34
cgctgctgcg ctattcggcg gcaactggaa caacacgtcg aactcgggtt ctcgcgctgc    60
gaactggaac aacgggccgt cgaactcgaa cgcgaacatc ggggcgcgcg gcgtctgtgc   120
ccatcaccct cttg                                                     134

<210> SEQ ID NO 35
<211> LENGTH: 134
<212> TYPE: DNA
```

-continued

<213> ORGANISM: Artificial Sequence
<220> FEATURE:
<223> OTHER INFORMATION: Modified TR strain 6405 AAA

<400> SEQUENCE: 35
cgctgctgcg ctattcggcg gcaactggaa caacacgtcg aactcgggtt ctcgcgctaa 60
aaactggaac aacgggccgt cgaactcgaa cgcgaacatc ggggcgcgcg gcgtctgtgc 120
ccatcacctt cttg 134

<210> SEQ ID NO 36
<211> LENGTH: 387
<212> TYPE: DNA
<213> ORGANISM: atd Wild type

<400> SEQUENCE: 36
atggaaccca tcgaggaagc gacaaagtgc tacgaccaaa tgctcattgt ggaacggtac 60
gaaagggtta tttcgtacct gtatcccatt gcgcaaagca tcccgaggaa gcacggcgtt 120
gcgcgggaaa tgttcctgaa gtgcctgctc gggcaggtcg aattattcat cgtggcgggc 180
aagtccaatc aggtgagcaa gctgtacgca gcggacgccg ggcttgccat gctgcgattt 240
tggttgcgct ttctcgcggg cattcagaaa ccgcacgcta tgacgccgca tcaggtcgag 300
acagcacaag tgctcatcgc cgaagtgggg cgcattctcg gctcctggat tgcccgcgtg 360
aatcgcaaag ggcaggctgg gaaataa 387

<210> SEQ ID NO 37
<211> LENGTH: 387
<212> TYPE: DNA
<213> ORGANISM: Artificial Sequence
<220> FEATURE:
<223> OTHER INFORMATION: Accessory tropism determinant - with stop codon

<400> SEQUENCE: 37
atggaaccca tcgaggaagc gacatagtgc tacgaccaaa tgctcattgt ggaacggtac 60
gaaagggtta tttcgtacct gtatcccatt gcgcaaagca tcccgaggaa gcacggcgtt 120
gcgcgggaaa tgttcctgaa gtgcctgctc gggcaggtcg aattattcat cgtggcgggc 180
aagtccaatc aggtgagcaa gctgtacgca gcggacgccg ggcttgccat gctgcgattt 240
tggttgcgct ttctcgcggg cattcagaaa ccgcacgcta tgacgccgca tcaggtcgag 300
acagcacaag tgctcatcgc cgaagtgggg cgcattctcg gctcctggat tgcccgcgtg 360
aatcgcaaag ggcaggctgg gaaataa 387

<210> SEQ ID NO 38
<211> LENGTH: 264
<212> TYPE: PRT
<213> ORGANISM: Aminoglycoside-3'-phosphotransferase-II (APH(3')-IIa)

<400> SEQUENCE: 38

Met Ile Glu Gln Asp Gly Leu His Ala Gly Ser Pro Ala Ala Trp Val
1 5 10 15

Glu Arg Leu Phe Gly Tyr Asp Trp Ala Gln Gln Thr Ile Gly Cys Ser
20 25 30

Asp Ala Ala Val Phe Arg Leu Ser Ala Gln Gly Arg Pro Val Leu Phe
35 40 45

Val Lys Thr Asp Leu Ser Gly Ala Leu Asn Glu Leu Gln Asp Glu Ala
50 55 60

Ala Arg Leu Ser Trp Leu Ala Thr Thr Gly Val Pro Cys Ala Ala Val

```
                65                  70                  75                  80
Leu Asp Val Val Thr Glu Ala Gly Arg Asp Trp Leu Leu Leu Gly Glu
                    85                  90                  95

Val Pro Gly Gln Asp Leu Leu Ser Ser His Leu Ala Pro Ala Glu Lys
                100                 105                 110

Val Ser Ile Met Ala Asp Ala Met Arg Arg Leu His Thr Leu Asp Pro
            115                 120                 125

Ala Thr Cys Pro Phe Asp His Gln Ala Lys His Arg Ile Glu Arg Ala
        130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260

<210> SEQ ID NO 39
<211> LENGTH: 131
<212> TYPE: DNA
<213> ORGANISM: APH(3')-IIa

<400> SEQUENCE: 39
aacctcgtga atacggtaac gccgctcccg ataagcagcg catcgccaac tatcgccttc    60
ttgacaagaa cttctgatcg aactcgacgc gaacatcggg gcgcgcggcg tctgtgccca   120
tcaccttctt g                                                        131

<210> SEQ ID NO 40
<211> LENGTH: 133
<212> TYPE: DNA
<213> ORGANISM: Artificial Sequence
<220> FEATURE:
<223> OTHER INFORMATION: Designed VR region for kanamycin resistance
      gene (APH(3')-IIa)

<400> SEQUENCE: 40
ttcctcgtgc tttaaggtat cgccgctccc gattcgcagc gcatcgcctt ctatcgcctt    60
cttgacgagt tcttctgatc gttctcgttc gcgttcttcg gggcgcgcgg cgtctgtgac   120
cacctgattc ttg                                                      133

<210> SEQ ID NO 41
<211> LENGTH: 329
<212> TYPE: PRT
<213> ORGANISM: Treponema denticola

<400> SEQUENCE: 41

Met Lys Asn Thr Asn Ser Lys Leu Lys Thr Lys Val Leu Asn Arg Ala
1               5                   10                  15
```

-continued

```
Ile Ser Ile Thr Ala Leu Leu Leu Ala Ala Gly Val Leu Leu Thr Gly
            20                  25                  30
Cys Pro Thr Gly Gln Gly Lys Ser Gly Gly Glu Ser Ser Glu Val
        35                  40                  45
Thr Pro Asn Thr Pro Val Asp Lys Thr Tyr Thr Val Gly Ser Val Glu
        50                  55                  60
Phe Thr Met Lys Gly Ile Ala Ala Val Asn Ala Gln Leu Gly His Asn
65                  70                  75                  80
Asp Tyr Ser Ile Asn Gln Pro His Thr Val Ser Leu Ser Ala Tyr Leu
                85                  90                  95
Ile Gly Glu Thr Glu Val Thr Gln Glu Leu Trp Gln Ala Val Met Gly
            100                 105                 110
Asn Asn Pro Ser His Phe Asn Gly Ser Pro Ala Val Gly Glu Thr Gln
        115                 120                 125
Gly Lys Arg Pro Val Glu Asn Val Asn Trp Tyr Gln Ala Ile Ala Phe
    130                 135                 140
Cys Asn Lys Leu Ser Ile Lys Leu Asn Leu Glu Pro Cys Tyr Thr Val
145                 150                 155                 160
Asn Val Gly Gly Asn Pro Val Asp Phe Ala Ala Leu Ser Phe Asp Gln
                165                 170                 175
Ile Pro Asp Ser Asn Asn Ala Asp Trp Asp Lys Ala Glu Leu Asp Ile
            180                 185                 190
Asn Lys Lys Gly Phe Arg Leu Pro Thr Glu Ala Glu Trp Glu Trp Ala
        195                 200                 205
Ala Lys Gly Gly Thr Asp Asp Lys Trp Ser Gly Thr Asn Thr Glu Ala
    210                 215                 220
Glu Leu Lys Asn Tyr Ala Trp Tyr Gly Ser Asn Ser Gly Ser Lys Thr
225                 230                 235                 240
His Glu Val Lys Lys Lys Pro Asn Trp Tyr Gly Leu Tyr Asp Ile
                245                 250                 255
Ala Gly Asn Val Ala Glu Trp Cys Trp Asp Trp Arg Ala Asp Ile His
            260                 265                 270
Thr Gly Asp Ser Phe Pro Gln Asp Tyr Pro Gly Pro Ala Ser Gly Ser
        275                 280                 285
Gly Arg Val Leu Arg Gly Gly Ser Trp Ala Gly Ser Ala Asp Tyr Cys
    290                 295                 300
Ala Val Gly Glu Arg Val Asn Ile Ser Pro Gly Val Arg Cys Ser Asp
305                 310                 315                 320
Leu Gly Phe Arg Leu Ala Cys Arg Pro
                325
```

<210> SEQ ID NO 42
<211> LENGTH: 6
<212> TYPE: PRT
<213> ORGANISM: Artificial Sequence
<220> FEATURE:
<223> OTHER INFORMATION: Recognition site of restriction enzyme HinCII

<400> SEQUENCE: 42

```
Gly Thr Tyr Arg Ala Cys
1               5
```

<210> SEQ ID NO 43
<211> LENGTH: 136
<212> TYPE: DNA
<213> ORGANISM: Treponema denticola -continued

```
<400> SEQUENCE: 43
ccgcgtcagg ctctaaccgt gttaaacgcg gcggcagctg gaacaacaac gcgaacaact      60
gcactgtagg caaacggaat aacaacagtc ctgacaacag gaacaacaat cttggcttcc     120
gcttggcttg tcggcc                                                     136

<210> SEQ ID NO 44
<211> LENGTH: 136
<212> TYPE: DNA
<213> ORGANISM: Treponema denticola

<400> SEQUENCE: 44
ccgcgtcagg ctctggccgt gttttacgcg gcggcagctg ggccggcagc gcggactact      60
gcgctgtagg cgaacgggtc aacatcagtc ctggcgtcag gtgcagcgat cttggcttcc     120
gcctggcttg ccggcc                                                     136

<210> SEQ ID NO 45
<211> LENGTH: 116
<212> TYPE: DNA
<213> ORGANISM: Treponema denticola

<400> SEQUENCE: 45
ccgcgtcagg ctctggccgt gttttacgcg gcggcagctg ggacaactac gcggagggct      60
gcactgtggg cacccggggt aacggcaacc ctggcaacag gggcaacctt cttggc         116

<210> SEQ ID NO 46
<211> LENGTH: 180
<212> TYPE: DNA
<213> ORGANISM: Bordetella bacteriophage

<400> SEQUENCE: 46
acggccaaca ctggcggccg cggatcggtg tacgcccagc ccgctgctgc gctattcggc      60
ggcgcctgga acggcacgtc gctctcgggt tctcgcgctg cgctctggta cagcgggccg     120
tcgttctcgt tcgcgttctt cggggcgcgc ggcgtctgtg accacctgat tcttgagtag     180

<210> SEQ ID NO 47
<211> LENGTH: 21
<212> TYPE: DNA
<213> ORGANISM: Bordetella bacteriophage

<400> SEQUENCE: 47
tctgtgacca cctgattctt g                                                21

<210> SEQ ID NO 48
<211> LENGTH: 21
<212> TYPE: DNA
<213> ORGANISM: Bordetella bacteriophage

<400> SEQUENCE: 48
tctgtgccca tcaccttctt g                                                21

<210> SEQ ID NO 49
<211> LENGTH: 22
<212> TYPE: DNA
<213> ORGANISM: Bordetella bacteriophage

<400> SEQUENCE: 49
aaaaaaaaaa aaaaaaaaaa aa                                               22
```

```
<210> SEQ ID NO 50
<211> LENGTH: 23
<212> TYPE: DNA
<213> ORGANISM: Bordetella bacteriophage

<400> SEQUENCE: 50
tgcaagggct cttaagtttt ttt                                              23

<210> SEQ ID NO 51
<211> LENGTH: 23
<212> TYPE: DNA
<213> ORGANISM: Bordetella bacteriophage

<400> SEQUENCE: 51
actaaatact ttaatctata aga                                              23

<210> SEQ ID NO 52
<211> LENGTH: 22
<212> TYPE: DNA
<213> ORGANISM: Bordetella bacteriophage

<400> SEQUENCE: 52
cctaagaccg cagaaaaaaa aa                                               22

<210> SEQ ID NO 53
<211> LENGTH: 22
<212> TYPE: DNA
<213> ORGANISM: Bordetella bacteriophage

<400> SEQUENCE: 53
cgcgaaatat ctctaaaaaa aa                                               22

<210> SEQ ID NO 54
<211> LENGTH: 22
<212> TYPE: DNA
<213> ORGANISM: Bordetella bacteriophage

<400> SEQUENCE: 54
ctctcaacat caaaaaaaaa aa                                               22

<210> SEQ ID NO 55
<211> LENGTH: 22
<212> TYPE: DNA
<213> ORGANISM: Bordetella bacteriophage

<400> SEQUENCE: 55
gcgcaaaaag caaaaaaaaa aa                                               22

<210> SEQ ID NO 56
<211> LENGTH: 22
<212> TYPE: DNA
<213> ORGANISM: Bordetella bacteriophage

<400> SEQUENCE: 56
gccgaaatat ctctaacaaa aa                                               22

<210> SEQ ID NO 57
<211> LENGTH: 22
<212> TYPE: DNA
<213> ORGANISM: Bordetella bacteriophage

<400> SEQUENCE: 57
gcgcagaaag caaaaaaaaa aa                                               22
```

<210> SEQ ID NO 58
<211> LENGTH: 22
<212> TYPE: DNA
<213> ORGANISM: Bordetella bacteriophage

<400> SEQUENCE: 58
cgagaaaaaa gagcaaaaaa aa                                              22

<210> SEQ ID NO 59
<211> LENGTH: 22
<212> TYPE: DNA
<213> ORGANISM: Bordetella bacteriophage

<400> SEQUENCE: 59
ccgaaaatca caaaataaaa aa                                              22

<210> SEQ ID NO 60
<211> LENGTH: 94
<212> TYPE: DNA
<213> ORGANISM: Bacteriophage BPP-1

<400> SEQUENCE: 60
cgctgctgcg ctattcggcg gcaactggaa caacacgtcg aactcgggtt ctcgagctgc     60
gaactggaac aacgggccgt cgaacgcgaa catc                                 94

<210> SEQ ID NO 61
<211> LENGTH: 100
<212> TYPE: DNA
<213> ORGANISM: Bacteriophage BPP-1

<400> SEQUENCE: 61
cgctgctgcg cttttcggcg gcgcctgggc caacacgtcg agctcgggtt ctcgggctgc     60
ggtctggtcc tacgggccgt cgctctcgta cgcgtacatc                          100

<210> SEQ ID NO 62
<211> LENGTH: 100
<212> TYPE: DNA
<213> ORGANISM: Bacteriophage BPP-1

<400> SEQUENCE: 62
cgctgctgcg ctattcggcg gcgcctggta cgccccgtcg ttctcgggtt ctcgggctgc     60
gtactggtac gccgggccgt cgtactcggt cgcgagcatc                          100

<210> SEQ ID NO 63
<211> LENGTH: 100
<212> TYPE: DNA
<213> ORGANISM: Bacteriophage BPP-1

<400> SEQUENCE: 63
cgctgctgcg ctgttcggcg gcagctggca ctacacgtcg aactcgggtt ctcgggctgc     60
gatctggtac tacgggccgt cgttctcggg cgcgagcgtc                          100

<210> SEQ ID NO 64
<211> LENGTH: 100
<212> TYPE: DNA
<213> ORGANISM: Bacteriophage BPP-1

<400> SEQUENCE: 64
cgctgctgcg ctattcggcg gctcctggta caacacgtcg aactcgggtt ctcgtgctgc     60

```
gtactggtac aacgggccgt cgttctcgtt cgcgttcttc                          100
```

<210> SEQ ID NO 65
<211> LENGTH: 100
<212> TYPE: DNA
<213> ORGANISM: Bacteriophage BPP-1

<400> SEQUENCE: 65

```
cgctgctgcg ctattcggcg gcagctggag caacacgtcg aactcgggtt ctcgggctgc    60
gtactggaac agcgggccgt cgttctcgtt cgcgttcttc                          100
```

<210> SEQ ID NO 66
<211> LENGTH: 100
<212> TYPE: DNA
<213> ORGANISM: Bacteriophage BPP-1

<400> SEQUENCE: 66

```
cgctgctgcg ctattcggcg gcgcctggac caacacgtcg aactcgggtt ctcgcgctgc    60
gaactggaac aacgggccgt cgaactcgaa cgcgaacatc                          100
```

<210> SEQ ID NO 67
<211> LENGTH: 100
<212> TYPE: DNA
<213> ORGANISM: Bacteriophage BPP-1

<400> SEQUENCE: 67

```
cgctgctgcg ctattcggcg gcgcctggtc caacacgtcg aactcgggtt ctcgcgctgc    60
gtactggccc tacgggccgt cgaactcgca cgcgtacgtc                          100
```

<210> SEQ ID NO 68
<211> LENGTH: 100
<212> TYPE: DNA
<213> ORGANISM: Bacteriophage BPP-1

<400> SEQUENCE: 68

```
cgctgctgcg ctattcggcg gcgcctggta caacacgtcg aactcgggtt ctcgcgctgc    60
gttctggtcc agcgggccgt cgtactcgta cgcgagcatc                          100
```

<210> SEQ ID NO 69
<211> LENGTH: 100
<212> TYPE: DNA
<213> ORGANISM: Bacteriophage BPP-1

<400> SEQUENCE: 69

```
cgctgctgcg ctattcggcg gcgcctggat caacacgtcg aactcgggtt ctcgcgctgc    60
gctctggtac tacgggccgt cggtctcgat cgcgaacatc                          100
```

<210> SEQ ID NO 70
<211> LENGTH: 100
<212> TYPE: DNA
<213> ORGANISM: Bacteriophage BPP-1

<400> SEQUENCE: 70

```
cgctgctgcg ctattcggcg gcgcctggaa ctacacgtcg aactcgggtt ctcgcgctgc    60
gatctggtac tacgggccgt cgaactcgaa cgcgagcatc                          100
```

<210> SEQ ID NO 71
<211> LENGTH: 100
<212> TYPE: DNA
<213> ORGANISM: Bacteriophage BPP-1

```
<400> SEQUENCE: 71
cgctgctgcg ctattcggcg gcgcctgggc ctacacgtcg atctcgggtt ctcgcgctgc    60
gtactggagc cacgggccgt cgaactcggc cgcgagcatc                         100

<210> SEQ ID NO 72
<211> LENGTH: 38
<212> TYPE: DNA
<213> ORGANISM: Bacteriophage BPP-1

<400> SEQUENCE: 72
aactggaaca acgggccgtc gaactcgaac gcgaacat                            38

<210> SEQ ID NO 73
<211> LENGTH: 38
<212> TYPE: DNA
<213> ORGANISM: Bacteriophage BPP-1

<400> SEQUENCE: 73
ctctggtaca gcgggccgtc gttctccttc gcgttctt                            38

<210> SEQ ID NO 74
<211> LENGTH: 38
<212> TYPE: DNA
<213> ORGANISM: Artificial Sequence
<220> FEATURE:
<223> OTHER INFORMATION: VR variant derived from delta 61 phage

<400> SEQUENCE: 74
ctctggtaca gcgggccgtc gttctcgggc gcgagcct                            38

<210> SEQ ID NO 75
<211> LENGTH: 38
<212> TYPE: DNA
<213> ORGANISM: Artificial Sequence
<220> FEATURE:
<223> OTHER INFORMATION: VR variant derived from delta 61 phage

<400> SEQUENCE: 75
ctctggtaca gcgggccgtc gttctcgtac gcgggcat                            38

<210> SEQ ID NO 76
<211> LENGTH: 38
<212> TYPE: DNA
<213> ORGANISM: Artificial Sequence
<220> FEATURE:
<223> OTHER INFORMATION: VR variant derived from delta 61 phage

<400> SEQUENCE: 76
ctctggtaca gcgggccgtc gtactcgtac gcgagcgt                            38

<210> SEQ ID NO 77
<211> LENGTH: 38
<212> TYPE: DNA
<213> ORGANISM: Artificial Sequence
<220> FEATURE:
<223> OTHER INFORMATION: VR variant derived from delta 61 phage

<400> SEQUENCE: 77
ctctggtaca gcgggccgtc gaactcgtac gcgtacat                            38

<210> SEQ ID NO 78
<211> LENGTH: 134
<212> TYPE: DNA
```

<213> ORGANISM: Bordetella phage

<400> SEQUENCE: 78

```
cgctgctgcg ctattcggcg gcaactggaa caacacggcg aactcgggtt ctcgcgctgc      60
gaactggaac aacgggccgt cgaactcgaa cgcgaacatc ggggcgcgcg gcgtctgtgc     120
ccatcacctt cttg                                                       134
```

<210> SEQ ID NO 79
<211> LENGTH: 139
<212> TYPE: DNA
<213> ORGANISM: Bordetella phage

<400> SEQUENCE: 79

```
cgctgctgcg ctattcggcg gcgcctggaa cggcgcggcg ctctcgggtt ctcgcgctgc      60
gctctggtac agcgggccgt cgttctcgtt cgcgttcttc ggggcgcgcg gcgtctgtga     120
ccacctgatt cttgagtag                                                  139
```

<210> SEQ ID NO 80
<211> LENGTH: 124
<212> TYPE: DNA
<213> ORGANISM: Vibrio harveyi phage

<400> SEQUENCE: 80

```
accgattccc gcttcgcggg ggcaactgga acaatggctc gaacgccggg ctgggcgcgc      60
tcaatctgaa caatgcgcgg tcgaactcga acaatagcat cggttttcgc cccgctcttg     120
atgt                                                                  124
```

<210> SEQ ID NO 81
<211> LENGTH: 128
<212> TYPE: DNA
<213> ORGANISM: Vibrio harveyi phage

<400> SEQUENCE: 81

```
accggttccc gcttcgcggg ggctactgga acaatggctc gagcgccggg ctgggcgcgc      60
tctatctgag ctatgcgcgg tcgaactcga acagtagcat cggttttcgc cccgctttct     120
ttgtgtaa                                                              128
```

<210> SEQ ID NO 82
<211> LENGTH: 109
<212> TYPE: DNA
<213> ORGANISM: Bifidobacterium Longum

<400> SEQUENCE: 82

```
ggtgcagcgc ttcggcaacc tcaggaacgg ggctgcctgc ggcgccttcg ccgtgaacct      60
cacgaacgac ctcgcgaatc gcaggtggaa catcggggc gcatatccg                  109
```

<210> SEQ ID NO 83
<211> LENGTH: 133
<212> TYPE: DNA
<213> ORGANISM: Bifidobacterium Longum

<400> SEQUENCE: 83

```
ggtgcggcgc ttcggcctcc tctgggacgg ggctgcctgc ggcgccttcg ccgtgtacct      60
cgcgaacgcc ctcgcgaatc gctgtggcac ctcgggggcc gccttttctg cgctcggtcg     120
cacgaaggct gag                                                        133
```

<210> SEQ ID NO 84
<211> LENGTH: 190
<212> TYPE: DNA
<213> ORGANISM: Bacteriodes thetaiotaomicron

<400> SEQUENCE: 84
ttccctgcgt cggggtatcg caactattcc aatggcgggg cgaacaacgt tggcagctac      60
ggctactgtt ggtcggcggt tccgaacaac cagaacaacg gtcgcaacct gaacttcaac     120
tcgtcgaacg tgaacccgtt gaacaacaac aatcgggcgt acgggtttgg ggtgcgttct     180
tcccaagaat                                                            190

<210> SEQ ID NO 85
<211> LENGTH: 192
<212> TYPE: DNA
<213> ORGANISM: Bacteriodes thetaiotaomicron

<400> SEQUENCE: 85
ttccctgcgt cggggtctcg cgactgttcc ggtggcgggg cgaacagcgt tggcttctac      60
ggcgtctgtt ggtcggcggt tccgtacagc cagtaccacg gttgcaccct ggacttctcc     120
tcgtcgtccg tgtacccgtt gctctactac tctcgggcgt gcgggtttgg gttgcgttct     180
tcccaagaat ag                                                         192

<210> SEQ ID NO 86
<211> LENGTH: 137
<212> TYPE: DNA
<213> ORGANISM: Treponema denticola

<400> SEQUENCE: 86
ccgcgtcagg ctctaaccga gttaaacgcg gcggcagctg gaacaacaac gcgaacaact      60
gcactgtagg caaacggaat aacaacagtc ctgacaacag gaacaacaat cttggcttcc     120
gcttggcttg tcggccc                                                    137

<210> SEQ ID NO 87
<211> LENGTH: 140
<212> TYPE: DNA
<213> ORGANISM: Treponema denticola

<400> SEQUENCE: 87
ccgcgtcagg ctctggccgt gttttacgcg gcggcagctg ggccggcagc gcggactact      60
gcgctgtagg cgaacgggtc aacatcagtc ctggcgtcag gtgcagcgat cttggcttcc     120
gcctggcttg ccggccttaa                                                 140

<210> SEQ ID NO 88
<211> LENGTH: 121
<212> TYPE: DNA
<213> ORGANISM: Trichodesmium erythraeum #1

<400> SEQUENCE: 88
gcggctcctg gaacaactat cctaggaggt gtcgctctgc gaaccgcaac aactataact      60
cggacgaggc ggacaacaac aatattggtt ttcgtcttgt gagtttcccc ccagcactct     120
t                                                                     121

<210> SEQ ID NO 89
<211> LENGTH: 126
<212> TYPE: DNA
<213> ORGANISM: Trichodesmium erythraeum #1

```
<400> SEQUENCE: 89
gcggctcctg gctcaactat ccttggtggt gtcgctctgc gtaccgctac gactttagct    60
cggacggggc ggtcatcatc aattttggtt ttcgtcttgt gagtttcccc ccaggactct   120
tgaata                                                              126

<210> SEQ ID NO 90
<211> LENGTH: 122
<212> TYPE: DNA
<213> ORGANISM: Trichodesmium erythraeum #1

<400> SEQUENCE: 90
gcggctcctg gtacgacttt ccttggtgtg tcgctctgcg ttccgcggct actatttctc    60
ggtcgaggcg gtcaacgact tgttggtttt tcgtcttgtg agtttccccc caggactcct   120
ga                                                                  122

<210> SEQ ID NO 91
<211> LENGTH: 150
<212> TYPE: DNA
<213> ORGANISM: Trichodesmium erythraeum #2

<400> SEQUENCE: 91
gctccgtggc ggtagctgga accacaattc tagacattgc cggagtgcca ggggcaacta    60
taaaaatgcc gacaacctca acaacaatag gggttttcga gtcatctcgt cttccccggt   120
ggtttctggc tttcattcct agtattcttc                                    150

<210> SEQ ID NO 92
<211> LENGTH: 150
<212> TYPE: DNA
<213> ORGANISM: Trichodesmium erythraeum #2

<400> SEQUENCE: 92
gctccgtggc ggttgctgga tccacaattc tagattttgc cggagtgcct ggcgcaacta    60
tctctatgcc gactacctct ccaacgatag gggttttcga gtcatctcct cttccccggt   120
ggtttctggc tttcattcct agtattcttc                                    150

<210> SEQ ID NO 93
<211> LENGTH: 138
<212> TYPE: DNA
<213> ORGANISM: Nostoc. spp. 7120 #1

<400> SEQUENCE: 93
ctgcggggcg gctcctggaa caacaatcct gaaaactgcc gttccgcgtc ccgcaacaac    60
aacaataggg cggagcgcga caacatcaac aacaatattg gttttcgtgt tgtctgcgcg   120
ttcgggagta ctcttcac                                                 138

<210> SEQ ID NO 94
<211> LENGTH: 141
<212> TYPE: DNA
<213> ORGANISM: Nostoc. spp. 7120 #1

<400> SEQUENCE: 94
ctgcggggcg gctcctggga cgaccttcct gaaggctgcc gttccgcgtc ccgcctcagc    60
ctcaataggg cggtgcgcga cctcatcctc tacagttttg gttttcgtgt tgtctgcgcg   120
ttcgggagga ttcttcagta g                                             141
```

<210> SEQ ID NO 95
<211> LENGTH: 141
<212> TYPE: DNA
<213> ORGANISM: Nostoc. spp. 7120 #1

<400> SEQUENCE: 95
ctgcggggcg gctcctggag ctcctctcct gtagtctgcc gttccgcgtc ccgcggcaac    60
aacgataggg cggggcgcgt ctaccgctac tacgctgttg gttttcgtgt tgtctgcgcg   120
ttcgggagga cttttcagta g                                             141

<210> SEQ ID NO 96
<211> LENGTH: 122
<212> TYPE: DNA
<213> ORGANISM: Nostoc. spp. 7120 #2

<400> SEQUENCE: 96
ctgctgcgcg gtggttcgtg gaacaacaat cccaggaatt gccgttcggc gaatcgcaac    60
aggaacgcgc gtgacaacag gaacaacaac gtaggttttc gggttgtggt tgtgcggggc   120
ag                                                                  122

<210> SEQ ID NO 97
<211> LENGTH: 132
<212> TYPE: DNA
<213> ORGANISM: Nostoc. spp. 7120 #2

<400> SEQUENCE: 97
ctgctgcgtg gtggttcgtg gaactactat cccaggggtt gccgttcgtt gagtcgcctc    60
agtaacacgc gcgacgacag gaacgagcgc gtgggttgtc gggttgtggt tgtgcggggc   120
aggctttctt ag                                                       132

<210> SEQ ID NO 98
<211> LENGTH: 137
<212> TYPE: DNA
<213> ORGANISM: Nostoc punctiforme

<400> SEQUENCE: 98
ctgcggggcg gttcctggat caacaatcct aaaaactgcc gttccgcgtc ccgcaacaac    60
aacaataggg cggagcgcga caacatcaac aacaatattg gttttcgtgt tgtctgcgcg   120
ttcgggatgt ctcttca                                                  137

<210> SEQ ID NO 99
<211> LENGTH: 141
<212> TYPE: DNA
<213> ORGANISM: Nostoc punctiforme

<400> SEQUENCE: 99
ctgcggggcg gttcctggtt caacaatcct gatttctgcc gttccgcgtc ccgcgtcatc    60
aacagttggg cggagcgcga caacgtcgtc agcaatgttg gttttcgtgt tgtctgcgcg   120
ttcgggagga ttcttcagta g                                             141

<210> SEQ ID NO 100
<211> LENGTH: 141
<212> TYPE: DNA
<213> ORGANISM: Nostoc punctiforme

<400> SEQUENCE: 100
ctgcggggcg gttcctggat cttcgatcct gattactgcc gttccgcgtc ccgcaacctc    60

-continued

```
agctataggg cggagcgcga cggcatcctc agcactcttg gttttcgtgt tgtctgcgcg    120
ttcgggagga ttcttcagta g                                              141
```

<210> SEQ ID NO 101
<211> LENGTH: 133
<212> TYPE: DNA
<213> ORGANISM: Artificial Sequence
<220> FEATURE:
<223> OTHER INFORMATION: Designed VR region for APH(3')-IIa

<400> SEQUENCE: 101

```
ttcctcgtgc tttacggtat cgccgctccc gattcgcagc gcatcgcctt ctatcgcctt     60
cttgacgagt tcttctgatc gttctcgttc gcgttcttcg gggcgcgcgg cgtctgtgac    120
cacctgattc ttg                                                       133
```

<210> SEQ ID NO 102
<211> LENGTH: 25
<212> TYPE: PRT
<213> ORGANISM: Artificial Sequence
<220> FEATURE:
<223> OTHER INFORMATION: Encoded kanamycin resistance fragment

<400> SEQUENCE: 102

```
Phe Leu Val Leu Tyr Gly Ile Ala Ala Pro Asp Ser Gln Arg Ile Ala
1               5                   10                  15

Phe Tyr Arg Leu Leu Asp Glu Phe Phe
            20                  25
```

<210> SEQ ID NO 103
<211> LENGTH: 18
<212> TYPE: PRT
<213> ORGANISM: Artificial Sequence
<220> FEATURE:
<223> OTHER INFORMATION: Hypothetical encoded peptide sequence

<400> SEQUENCE: 103

```
Ser Phe Ser Phe Ala Phe Phe Gly Ala Arg Gly Val Cys Asp His Leu
1               5                   10                  15

Ile Leu
```